US012751854B2

(12) United States Patent
Metzger et al.

(10) Patent No.: US 12,751,854 B2
(45) Date of Patent: *Oct. 6, 2026

(54) FLUID COLLECTION DEVICES, FLUID COLLECTION SYSTEMS INCLUDING THE SAME, AND METHODS OF USING THE SAME

(71) Applicant: PUREWICK CORPORATION, El Cajon, CA (US)

(72) Inventors: Stephanie Metzger, Oyster Bay, NY (US); Candace Scalf, Springboro, OH (US); Caroline Ottinger, North Bend, WA (US); Ashley Marie Johannes, Atlanta, GA (US); Pranav Challa, Atlanta, GA (US)

(73) Assignee: PUREWICK CORPORATION, Covington, GA (US)

( * ) Notice: Subject to any disclaimer, the term of this patent is extended or adjusted under 35 U.S.C. 154(b) by 990 days.

This patent is subject to a terminal disclaimer.

(21) Appl. No.: 17/614,173

(22) PCT Filed: May 15, 2020

(86) PCT No.: PCT/US2020/033122

§ 371 (c)(1),
(2) Date: Nov. 24, 2021

(87) PCT Pub. No.: WO2020/242790

PCT Pub. Date: Dec. 3, 2020

(65) Prior Publication Data

US 2022/0218510 A1 Jul. 14, 2022

Related U.S. Application Data

(60) Provisional application No. 62/853,279, filed on May 28, 2019.

(51) Int. Cl.
*A61F 5/443* (2006.01)
*A61F 5/44* (2006.01)
(Continued)

(52) U.S. Cl.
CPC ............ *A61F 5/443* (2013.01); *A61F 5/4404* (2013.01); *A61F 5/453* (2013.01); *A61F 5/455* (2013.01); *A61M 1/60* (2021.05)

(58) Field of Classification Search
CPC ........ A61F 5/443; A61F 5/4404; A61F 5/453; A61F 5/455; A61M 1/60
See application file for complete search history.

(56) References Cited

U.S. PATENT DOCUMENTS 976,883 A 11/1910 Keagy et al.
1,229,423 A 6/1917 Eckenrode
(Continued)

FOREIGN PATENT DOCUMENTS

AU 2022349367 A1 4/2024
CA 2335223 A1 1/2000
(Continued)

OTHER PUBLICATIONS

KR 20090072069 A (Year: 2009).*
(Continued)

*Primary Examiner* — Andrew J Mensh
*Assistant Examiner* — Hans Kaliher
(74) *Attorney, Agent, or Firm* — Ballard Spahr LLP

(57) ABSTRACT

An example urinary collection device includes a fluid impermeable barrier defining a chamber, an opening, and an outlet. The opening and the outlet fluid to enter and leave the chamber, respectively. The urinary collection device also includes a fluid permeable membrane extending across the opening. The urinary collection device includes a fluid receiving portion that includes the portions of the fluid
(Continued)

impermeable barrier that defines the opening. The fluid receiving portion is configured to be positioned such that the opening is disposed adjacent to the urethral opening of the individual (e.g., a buried penis). The urinary collection device also includes an longitudinal portion extending from the fluid receiving portion. The longitudinal portion is configured to be positioned adjacent to or near the perineum of the individual (e.g., positioned between the thighs of the individual).

24 Claims, 5 Drawing Sheets

(51) Int. Cl.
*A61F 5/453* (2006.01)
*A61F 5/455* (2006.01)
*A61M 1/00* (2006.01)

(56) References Cited

U.S. PATENT DOCUMENTS 2,789,560 A 4/1957 Weimer
3,114,916 A 12/1963 Hadley
3,356,091 A 12/1967 Patterson
3,368,564 A 2/1968 Selix
3,369,940 A 2/1968 Slautterback
3,411,504 A 11/1968 Glassman
3,434,565 A 3/1969 Fischer
3,447,536 A 6/1969 Snyder
3,608,552 A 9/1971 Broerman
3,720,554 A 3/1973 Stumpf
3,721,243 A 3/1973 Greth et al.
3,727,788 A 4/1973 Holbrook
3,730,411 A 5/1973 Brockmuller
3,742,953 A 7/1973 Lee
3,931,650 A 1/1976 Miller
3,931,819 A 1/1976 Weedle
3,964,786 A 6/1976 Mashuda
4,006,793 A 2/1977 Robinson
4,022,211 A 5/1977 Timmons et al.
4,023,216 A 5/1977 Li
4,031,897 A 6/1977 Graetz
4,042,337 A 8/1977 Griffith
4,069,817 A 1/1978 Fenole et al.
4,084,589 A 4/1978 Kulvi
4,140,739 A 2/1979 Cotten
4,197,849 A 4/1980 Bostick
D255,935 S 7/1980 Cullis et al.
4,280,498 A 7/1981 Jensen
4,345,341 A 8/1982 Saito
4,349,029 A 9/1982 Mott
4,356,012 A 10/1982 Hofstetter
4,372,299 A 2/1983 Fixel
4,421,511 A 12/1983 Steer et al.
4,457,758 A 7/1984 Norton
4,512,771 A 4/1985 Norton
4,533,354 A 8/1985 Jensen
4,533,357 A 8/1985 Hall
4,568,341 A 2/1986 Mitchell et al.
4,583,983 A 4/1986 Einhorn et al.
4,681,572 A 7/1987 Tokarz et al.
4,692,160 A * 9/1987 Nussbaumer ........... A61F 5/455
604/331
4,759,753 A 7/1988 Schneider et al.
4,775,458 A 10/1988 Forester
4,846,824 A 7/1989 Lassen et al.
4,857,064 A 8/1989 Mendoza
4,872,299 A 10/1989 Troutner et al.
4,875,898 A 10/1989 Eakin
4,886,508 A * 12/1989 Washington ............ A61F 5/455
604/347
4,895,140 A 1/1990 Bellak
D306,759 S 3/1990 D'Alo
4,911,262 A 3/1990 Tani et al.
4,930,997 A 6/1990 Bennett
5,030,229 A 7/1991 Yang
5,102,404 A 4/1992 Goldberg et al.
5,134,994 A 8/1992 Say
5,137,033 A 8/1992 Norton
5,199,444 A 4/1993 Wheeler
5,234,419 A 8/1993 Bryant et al.
5,295,979 A 3/1994 DeLaurentis et al.
5,330,457 A 7/1994 Cohen
5,334,174 A 8/1994 Street
5,334,176 A 8/1994 Buenger et al.
D354,129 S 1/1995 Salvadori
D354,560 S 1/1995 Chase
5,397,315 A 3/1995 Schmidt et al.
5,423,788 A 6/1995 Rollins et al.
5,437,836 A 8/1995 Yamada
5,455,091 A 10/1995 Oreglia et al.
5,525,407 A 6/1996 Yang
5,614,699 A 3/1997 Yashiro et al.
5,632,736 A 5/1997 Block
D380,543 S 7/1997 Piontek et al.
5,662,633 A 9/1997 Doak et al.
5,681,297 A 10/1997 Hashimoto et al.
5,695,487 A 12/1997 Cohen et al.
5,735,837 A 4/1998 Ishikawa
5,873,869 A 2/1999 Hammons et al.
5,895,349 A 4/1999 Tihon
5,956,782 A 9/1999 Olguin
6,007,524 A 12/1999 Schneider
D421,307 S 2/2000 Harmanoglu
6,061,905 A 5/2000 Logic
6,316,688 B1 11/2001 Hammons et al.
6,395,956 B1 5/2002 Glasgow et al.
6,417,750 B1 7/2002 Sohn
6,461,340 B1 10/2002 Lenker et al.
6,526,603 B1 3/2003 Murphy
6,848,719 B2 2/2005 Rowley
6,878,647 B1 4/2005 Rezai et al.
6,918,899 B2 7/2005 Harvie
7,087,043 B2 8/2006 Dolan
7,803,144 B1 9/2010 Vollrath
7,981,087 B2 7/2011 Gesler, III
8,156,941 B1 4/2012 Simms
8,167,860 B1 5/2012 Siegel
8,551,062 B2 10/2013 Kay
8,702,667 B1 4/2014 Johnson
8,740,852 B2 6/2014 Aviles
9,415,191 B2 8/2016 Aviles
9,737,433 B2 8/2017 Joh
D806,236 S 12/2017 Lin
9,968,908 B2 5/2018 Ladrech et al.
10,010,393 B1 7/2018 Nguyen et al.
10,376,406 B2 * 8/2019 Newton .................. A61F 5/453
10,806,623 B2 10/2020 VanMiddendorp et al.
10,857,025 B2 * 12/2020 Davis ...................... A61F 5/455
11,002,165 B2 5/2021 Poulin
11,020,567 B2 6/2021 Rule et al.
11,199,116 B2 12/2021 Ostromecki et al.
D941,998 S 1/2022 Tretheway et al.
11,813,189 B2 11/2023 Hussey et al.
11,911,160 B2 2/2024 Woodard et al.
12,064,372 B2 * 8/2024 Godinez ................. A61F 5/455
12,070,432 B2 8/2024 Tourchak et al.
12,121,468 B2 10/2024 Sanchez et al.
D1,054,019 S 12/2024 Miyawaki
D1,059,585 S 1/2025 Miyawaki
D1,059,586 S 1/2025 Miyawaki
12,186,229 B2 1/2025 Davis et al.
12,193,962 B2 1/2025 Newton et al.
D1,067,424 S 3/2025 Naughton et al.
12,245,966 B2 3/2025 Newton
12,274,638 B2 4/2025 Spector
D1,074,995 S 5/2025 Laffay et al.
12,324,765 B2 6/2025 Sanchez et al.
12,350,190 B2 * 7/2025 Hughett, Sr. ........... A61F 5/453
D1,104,255 S 12/2025 Hanna et al.
D1,107,222 S 12/2025 Ecklund et al.
2001/0037098 A1 11/2001 Snyder

(56) References Cited

U.S. PATENT DOCUMENTS

2002/0033200 A1 3/2002 Alex et al.
2002/0042945 A1 4/2002 Sands
2003/0018309 A1 1/2003 Breznock
2003/0074724 A1 4/2003 Sands
2003/0129178 A1 7/2003 Wegman et al.
2004/0002687 A1 1/2004 Burns et al.
2004/0098794 A1 5/2004 Ernest et al.
2004/0102753 A1 5/2004 Butler
2004/0147895 A1 7/2004 Mizutani et al.
2004/0181201 A1 9/2004 Mizutani et al.
2004/0187200 A1 9/2004 Otto et al.
2004/0194792 A1 10/2004 Zhuang et al.
2005/0131361 A1 6/2005 Miskie
2005/0137560 A1 6/2005 Mizutani et al.
2005/0137561 A1 6/2005 Mizutani et al.
2005/0148984 A1 7/2005 Lindsay et al.
2005/0215969 A1 9/2005 Mizutani et al.
2005/0273069 A1 12/2005 Mizutani et al.
2005/0277903 A1 12/2005 Mizutani et al.
2006/0005307 A1* 1/2006 Arguelles ................ A61F 5/455 4/144.1
2006/0079852 A1 4/2006 Bubb et al.
2006/0100596 A1 5/2006 Miskie
2006/0113334 A1 6/2006 Mikhail et al.
2006/0166350 A1 7/2006 Lowe et al.
2007/0025886 A1 2/2007 Yong
2007/0270716 A1 11/2007 Wu et al.
2008/0077099 A1 3/2008 House
2008/0140033 A1 6/2008 Burgess et al.
2008/0200884 A1 8/2008 Perkins et al.
2009/0199857 A1 8/2009 Peake et al.
2009/0226541 A1 9/2009 Scholz et al.
2009/0247968 A1 10/2009 Brooks et al.
2009/0254040 A1 10/2009 Bierman et al.
2009/0306610 A1 12/2009 Van Den Heuvel et al.
2010/0030189 A1 2/2010 Fleming
2010/0031429 A1 2/2010 Kim et al.
2010/0032789 A1 2/2010 Schoen et al.
2010/0234820 A1* 9/2010 Tsai ........................ A61M 1/87 604/385.03
2011/0152842 A1 6/2011 Graffam et al.
2011/0198904 A1 8/2011 Thomas et al.
2012/0004079 A1 1/2012 Hyacinth
2012/0103347 A1* 5/2012 Wheaton ................. A61F 5/453 128/885
2012/0209225 A1 8/2012 Hu et al.
2012/0215187 A1 8/2012 Tippet et al.
2013/0019374 A1 1/2013 Schwartz
2013/0036544 A1 2/2013 Lee et al.
2013/0046258 A1 2/2013 Chambers
2013/0144240 A1 6/2013 Ellis
2013/0158494 A1 6/2013 Ong et al.
2013/0165880 A1 6/2013 Amos et al.
2013/0211385 A1 8/2013 Lazarus
2013/0274711 A1 10/2013 O'Day
2013/0324954 A1 12/2013 Friedrich
2014/0039440 A1 2/2014 Doescher
2014/0058347 A1 2/2014 Marquette
2014/0230831 A1 8/2014 Zaltsberg et al.
2014/0257231 A1 9/2014 Wang et al.
2015/0267862 A1 9/2015 Mishler
2015/0290421 A1 10/2015 Glickman et al.
2015/0359996 A1 12/2015 Arora et al.
2015/0374535 A1 12/2015 Davis et al.
2016/0008193 A1 1/2016 Schulke
2016/0051395 A1 2/2016 Ugarte M.D.
2016/0135792 A1 5/2016 Cai
2016/0136338 A1 5/2016 Lee et al.
2016/0327553 A1 11/2016 Edwards et al.
2016/0374848 A1* 12/2016 Sanchez .................. A61F 5/453 604/319
2017/0042724 A1 2/2017 Ugarte
2017/0049605 A1 2/2017 Wisniewski
2017/0107312 A1 4/2017 Hinayama et al.
2017/0281399 A1* 10/2017 VanMiddendorp ..... A61M 1/80
2017/0281419 A1 10/2017 Pintado
2017/0340489 A1 11/2017 Yamada
2018/0149635 A1 5/2018 Abir
2018/0169281 A1 6/2018 Russell et al.
2018/0214297 A1 8/2018 Hughett et al.
2018/0215649 A1 8/2018 Wada et al.
2018/0221216 A1 8/2018 Benz et al.
2018/0229014 A1 8/2018 Guirguis et al.
2018/0280236 A1 10/2018 Ludin et al.
2019/0001029 A1 1/2019 Davie et al.
2019/0029869 A1 1/2019 Huchthausen
2019/0038451 A1 2/2019 Harvie
2019/0060138 A1 2/2019 Marquez et al.
2019/0133126 A1 5/2019 Modak et al.
2019/0226189 A1 7/2019 Braxton
2019/0365303 A1 12/2019 Bullington et al.
2020/0040561 A1 2/2020 Sugawara
2020/0187918 A1 6/2020 Wiygul
2020/0352774 A1 11/2020 Rabinowitz et al.
2020/0384242 A1 12/2020 Havard et al.
2020/0398024 A1 12/2020 Fletter et al.
2020/0405523 A1 12/2020 Obst et al.
2021/0007910 A1 1/2021 Furukawa
2021/0186744 A1 6/2021 Spector
2021/0206144 A1 7/2021 Ewell
2021/0211568 A1 7/2021 Zhou et al.
2021/0290464 A1 9/2021 Furuta
2021/0315726 A1 10/2021 Lin
2021/0353449 A1 11/2021 Sharma et al.
2022/0015958 A1 1/2022 Ito
2022/0026546 A1 1/2022 Aono et al.
2022/0031290 A1 2/2022 Weed
2022/0062025 A1 3/2022 Shields et al.
2022/0118165 A1 4/2022 Knapp et al.
2022/0280710 A1 9/2022 Agrawal et al.
2022/0287691 A1 9/2022 Wormser et al.
2022/0287867 A1 9/2022 Jones et al.
2022/0339023 A1 10/2022 Davis et al.
2022/0387693 A1 12/2022 Bannwart et al.
2022/0401252 A1 12/2022 Warren
2022/0409419 A1 12/2022 Garvey et al.
2023/0091118 A1 3/2023 Watson
2023/0190511 A1 6/2023 Sharma et al.
2023/0277360 A1 9/2023 Lambert et al.
2023/0389900 A1 12/2023 Xie et al.
2024/0033148 A1 2/2024 Gordon et al.
2024/0058157 A1 2/2024 Davis
2024/0058160 A1 2/2024 Young Joyner et al.
2024/0058520 A1 2/2024 Yin et al.
2024/0082044 A1 3/2024 Nguyen et al.
2024/0108268 A1 4/2024 Woodard et al.
2024/0122773 A1 4/2024 Nguyen et al.
2024/0130885 A1 4/2024 Young Joyner et al.
2024/0156633 A1 5/2024 Fallows et al.
2024/0164935 A1 5/2024 Newton
2024/0252343 A1 8/2024 Voda
2024/0268986 A1 8/2024 Barnes et al.
2024/0268989 A1 8/2024 Martin et al.
2024/0268991 A1 8/2024 Davis
2024/0269027 A1 8/2024 Tourchak et al.
2024/0285425 A1 8/2024 Donohoe et al.
2024/0325190 A1 10/2024 Minchew et al.
2024/0341998 A1 10/2024 Julian et al.
2024/0358539 A1 10/2024 Gallup
2024/0358542 A1 10/2024 Richardson et al.
2024/0374414 A1 11/2024 Richardson et al.
2025/0009552 A1 1/2025 Blabas et al.
2025/0073055 A1 3/2025 Ecklund et al.
2025/0107920 A1 4/2025 Fallows et al.
2025/0107921 A1 4/2025 Sanchez et al.
2025/0367358 A1 12/2025 Smith et al.

FOREIGN PATENT DOCUMENTS

CA 3031934 A1 2/2018
CA 3144181 A1 1/2021
CA 3188651 A1 7/2023
CN 1579348 A 2/2005
CN 1638708 A 7/2005

(56) References Cited

FOREIGN PATENT DOCUMENTS

| | | | | |
|---|---|---|---|---|
| CN | 105451607 | A | 3/2016 | |
| CN | 106137631 | A | 11/2016 | |
| CN | 207785556 | U | 8/2018 | |
| CN | 110171118 | A | 8/2019 | |
| CN | 111465375 | A | 7/2020 | |
| CN | 213490035 | U | 6/2021 | |
| DE | 3104356 | A1 | 9/1982 | |
| DE | 202005013173 | U1 | 6/2006 | |
| DE | 202006018506 | U1 | 3/2007 | |
| DE | 102018118570 | A1 | 2/2020 | |
| EP | 0220962 | A1 | 5/1987 | |
| EP | 0483730 | A1 | 5/1992 | |
| EP | 0711536 | A1 | 5/1996 | |
| EP | 0680296 | B1 | 5/1997 | |
| EP | 0945231 | A2 | 9/1999 | |
| EP | 2470251 | B1 | 12/2014 | |
| EP | 3777801 | A1 | 2/2021 | |
| EP | 3749230 | B1 | 3/2023 | |
| EP | 4192402 | A1 | 6/2023 | |
| EP | 4218702 | A1 | 8/2023 | |
| EP | 3624742 | B1 | 1/2024 | |
| EP | 4215134 | B1 | 1/2025 | |
| EP | 4494611 | A2 | 1/2025 | |
| EP | 4527361 | A2 | 3/2025 | |
| FR | 2294812 | A1 | 7/1976 | |
| FR | 2826704 | A1 | 1/2003 | |
| GB | 0873045 | A | 7/1961 | |
| GB | 996370 | A | 6/1965 | |
| GB | 1011517 | A | 12/1965 | |
| GB | 2415386 | A | 12/2005 | |
| JP | S56152629 | U | 11/1981 | |
| JP | S58130026 | A | 8/1983 | |
| JP | S59118161 | A | 7/1984 | |
| JP | S61502100 | A | 9/1986 | |
| JP | H0515928 | U | 3/1993 | |
| JP | H0625981 | U | 4/1994 | |
| JP | H08117271 | A | 5/1996 | |
| JP | H08510924 | A | 11/1996 | |
| JP | 2686634 | B2 | 12/1997 | |
| JP | H1038669 | A | 2/1998 | |
| JP | 2000152953 | A | 6/2000 | |
| JP | 2002502667 | A | 1/2002 | |
| JP | 2002102285 | A | 4/2002 | |
| JP | 2003227004 | A | 8/2003 | |
| JP | 2004267400 | A | 9/2004 | |
| JP | 2005518901 | A | 6/2005 | |
| JP | 2006136491 | A | 6/2006 | |
| JP | 2008278928 | A | 11/2008 | |
| JP | 2009500111 | A | 1/2009 | |
| JP | 2010166954 | A | 8/2010 | |
| JP | 2011522584 | A | 8/2011 | |
| JP | 2011202664 | A | 10/2011 | |
| JP | 2012522014 | A | 9/2012 | |
| JP | 3208707 | U | 2/2017 | |
| JP | 3209321 | U | 3/2017 | |
| JP | 2017070400 | A | 4/2017 | |
| JP | 2017127596 | A | 7/2017 | |
| JP | 2019010375 | A | 1/2019 | |
| JP | 2020510464 | A | 4/2020 | |
| JP | 2020124425 | A | 8/2020 | |
| JP | 2021007472 | A | 1/2021 | |
| JP | 2021041145 | A | 3/2021 | |
| JP | 2021074491 | A | 5/2021 | |
| JP | 2021520952 | A | 8/2021 | |
| JP | 2021522019 | A | 8/2021 | |
| JP | 2022554252 | A | 12/2022 | |
| KR | 20090072069 | A * | 7/2009 | ............ A61F 5/455 |
| KR | 101035745 | B1 | 5/2011 | |
| KR | 20180022173 | A | 3/2018 | |
| KR | 101976679 | B1 | 5/2019 | |
| KR | 101998130 | B1 | 7/2019 | |
| KR | 20230034343 | A | 3/2023 | |
| TW | 408207 | B | 10/2000 | |
| TW | 202123903 | A | 7/2021 | |
| WO | 9416914 | A1 | 8/1994 | |
| WO | 03015671 | A1 | 2/2003 | |
| WO | 2005003725 | A2 | 1/2005 | |
| WO | 2005060558 | A2 | 7/2005 | |
| WO | 2017100511 | A1 | 6/2017 | |
| WO | 2018200721 | A1 | 11/2018 | |
| WO | 2019038732 | A1 | 2/2019 | |
| WO | 2019212950 | A1 | 11/2019 | |
| WO | 2020033752 | A1 | 2/2020 | |
| WO | 2021016056 | A1 | 1/2021 | |
| WO | 2022029662 | A1 | 2/2022 | |
| WO | 2022051220 | A1 | 3/2022 | |
| WO | 2022150290 | A1 | 7/2022 | |
| WO | 2022173803 | A1 | 8/2022 | |
| WO | 2022251184 | A1 | 12/2022 | |
| WO | 2022251425 | A1 | 12/2022 | |
| WO | 2022271783 | A1 | 12/2022 | |
| WO | 2023018656 | A1 | 2/2023 | |
| WO | 2023018657 | A1 | 2/2023 | |
| WO | 2023049156 | A1 | 3/2023 | |
| WO | 2023146529 | A1 | 8/2023 | |
| WO | 2023163725 | A1 | 8/2023 | |
| WO | 2024043871 | A1 | 2/2024 | |
| WO | 2024253655 | A1 | 12/2024 | |
| WO | 2025034959 | A1 | 2/2025 | |
| WO | 2025038087 | A1 | 2/2025 | |
| WO | 2025038088 | A1 | 2/2025 | |
| WO | 2025048789 | A1 | 3/2025 | |
| WO | 2025071622 | A1 | 4/2025 | |
| WO | 2025179267 | A1 | 8/2025 | |
| WO | 2026035497 | A1 | 2/2026 | |

OTHER PUBLICATIONS

International Search Report and Written Opinion from International Application No. PCT/US2020/033122 mailed Aug. 31, 2020.

“Proximate Definition & Meaning” <https://www.merriam-webster.com/dictionary/> 2025.

“Surface Energy Data for Cellulose acetate, CAS # 9004-35-7”, Diviersified Enterprises, 2009, 1 page.

“Tube Definition & Meaning” Merriam Webster Dictionary, 2025, <https://www.merriam-webster.com/dictionary/tube>.

Advisory Action for U.S. Appl. No. 16/452,258 mailed May 5, 2025.

Advisory Action for U.S. Appl. No. 17/378,015 mailed Oct. 28, 2025.

Advisory Action for U.S. Appl. No. 17/394,055 mailed Jan. 9, 2026.

Advisory Action for U.S. Appl. No. 17/446,256 mailed Nov. 6, 2025.

Advisory Action for U.S. Appl. No. 17/446,654 mailed Feb. 28, 2025.

Advisory Action for U.S. Appl. No. 17/451,345 mailed May 13, 2025.

Advisory Action for U.S. Appl. No. 17/595,747 mailed Mar. 17, 2025.

Advisory Action for U.S. Appl. No. 17/653,314 mailed Apr. 8, 2025.

Advisory Action for U.S. Appl. No. 17/655,464 mailed Feb. 25, 2025.

Advisory Action for U.S. Appl. No. 17/664,487 mailed Apr. 24, 2025.

Advisory Action for U.S. Appl. No. 17/757,311 mailed Jul. 2, 2025.

Advisory Action for U.S. Appl. No. 18/265,736 mailed Mar. 4, 2026.

Corrected Notice of Allowability for U.S. Appl. No. 17/444,792 mailed Jun. 24, 2025.

Corrected Notice of Allowability for U.S. Appl. No. 17/653,314 mailed Oct. 29, 2025.

Corrected Notice of Allowability for U.S. Appl. No. 17/754,736 mailed Feb. 12, 2026.

Corrected Notice of Allowability for U.S. Appl. No. 17/808,354 mailed Nov. 25, 2025.

Corrected Notice of Allowability for U.S. Appl. No. 17/996,253 mailed Apr. 28, 2025.

Corrected Notice of Allowability for U.S. Appl. No. 18/134,857 mailed Mar. 14, 2025.

(56) References Cited

OTHER PUBLICATIONS

Corrected Notice of Allowability for U.S. Appl. No. 18/260,122 mailed Aug. 11, 2025.
Corrected Notice of Allowability for U.S. Appl. No. 18/264,004 mailed Feb. 10, 2026.
Corrected Notice of Allowability for U.S. Appl. No. 18/264,004 mailed Feb. 3, 2026.
Di Mauro, et al., "Penile length and circumference dimensions: A large study in young Italian men" Reconstructive Urology, Men's Health Working Parties of the European Association of Urology (EAU) Young Academic Urologists (YAU). pp. 1-7, Mar. 8, 2021.
Final Office Action for U.S. Appl. No. 16/452,258 mailed Feb. 11, 2026.
Final Office Action for U.S. Appl. No. 17/051,600 mailed Aug. 6, 2025.
Final Office Action for U.S. Appl. No. 17/378,015 mailed Jun. 18, 2025.
Final Office Action for U.S. Appl. No. 17/394,055 mailed Sep. 24, 2025.
Final Office Action for U.S. Appl. No. 17/446,256 mailed Jun. 11, 2025.
Final Office Action for U.S. Appl. No. 17/446,654 mailed Dec. 22, 2025.
Final Office Action for U.S. Appl. No. 17/451,345 mailed Feb. 6, 2025.
Final Office Action for U.S. Appl. No. 17/595,747 mailed Feb. 19, 2026.
Final Office Action for U.S. Appl. No. 17/597,408 mailed Mar. 24, 2025.
Final Office Action for U.S. Appl. No. 17/625,941 mailed Feb. 18, 2025.
Final Office Action for U.S. Appl. No. 17/628,411 mailed Apr. 30, 2025.
Final Office Action for U.S. Appl. No. 17/631,619 mailed Oct. 1, 2025.
Final Office Action for U.S. Appl. No. 17/653,137 mailed Jun. 25, 2025.
Final Office Action for U.S. Appl. No. 17/653,314 mailed Jan. 30, 2025.
Final Office Action for U.S. Appl. No. 17/653,920 mailed Apr. 24, 2025.
Final Office Action for U.S. Appl. No. 17/655,464 mailed Feb. 17, 2026.
Final Office Action for U.S. Appl. No. 17/664,487 mailed Jan. 5, 2026.
Final Office Action for U.S. Appl. No. 17/756,201 mailed Dec. 30, 2025.
Final Office Action for U.S. Appl. No. 17/757,311 mailed Mar. 31, 2025.
Final Office Action for U.S. Appl. No. 17/759,697 mailed Jun. 4, 2025.
Final Office Action for U.S. Appl. No. 17/808,354 mailed Jun. 13, 2025.
Final Office Action for U.S. Appl. No. 17/809,083 mailed Jan. 23, 2026.
Final Office Action for U.S. Appl. No. 17/907,125 mailed Apr. 30, 2025.
Final Office Action for U.S. Appl. No. 17/929,887, filed Jan. 13, 2026.
Final Office Action for U.S. Appl. No. 17/933,590 mailed Feb. 19, 2026.
Final Office Action for U.S. Appl. No. 18/003,029 mailed Nov. 26, 2025.
Final Office Action for U.S. Appl. No. 18/006,807 mailed Dec. 23, 2025.
Final Office Action for U.S. Appl. No. 18/042,842 mailed Jan. 27, 2026.
Final Office Action for U.S. Appl. No. 18/043,618 mailed Nov. 26, 2025.
Final Office Action for U.S. Appl. No. 18/139,523 mailed May 8, 2025.
Final Office Action for U.S. Appl. No. 18/164,800 mailed Dec. 5, 2025.
Final Office Action for U.S. Appl. No. 18/247,986 mailed Jan. 7, 2026.
Final Office Action for U.S. Appl. No. 18/265,736 mailed Dec. 1, 2025.
Foamtech, "Foam Packaging Isnert: Best Selection Guide", https://web/archive.org/web/20170922162235/http://www.foamtechchina/com:80/foam-packaging-insert/, Sep. 22, 2017, 25 pages.
International Search Report and Written Opinion from International Application No. PCT/US2023/031432 mailed Feb. 29, 2024.
International Search Report and Written Opinion from International Application No. PCT/US2023/036875 mailed May 31, 2024.
International Search Report and Written Opinion from International Application No. PCT/US2023/077205 mailed Jul. 19, 2024.
International Search Report and Written Opinion from International Application No. PCT/US2024/053681 mailed Jan. 27, 2025.
International Search Report and Written Opinion from International Application No. PCT/US2024/058598 mailed Mar. 28, 2025.
International Search Report and Written Opinion from International Application No. PCT/US2025/018907 mailed May 16, 2025.
International Search Report and Written Opinion from International Application No. PCT/US2025/018909 mailed May 20, 2025.
International Search Report and Written Opinion from International Application No. PCT/US2025/018913 mailed Jun. 18, 2025.
Issue Notification for U.S. Appl. No. 16/433,773 mailed Jan. 21, 2026.
Issue Notification for U.S. Appl. No. 16/478,180 mailed Mar. 5, 2025.
Issue Notification for U.S. Appl. No. 16/904,868 mailed Apr. 30, 2025.
Issue Notification for U.S. Appl. No. 17/051,399 mailed Mar. 4, 2026.
Issue Notification for U.S. Appl. No. 17/051,585 mailed Mar. 26, 2025.
Issue Notification for U.S. Appl. No. 17/444,792 mailed Jun. 25, 2025.
Issue Notification for U.S. Appl. No. 17/451,354 mailed Feb. 25, 2026.
Issue Notification for U.S. Appl. No. 17/501,591 mailed Mar. 5, 2025.
Issue Notification for U.S. Appl. No. 17/529,769 mailed Feb. 19, 2025.
Issue Notification for U.S. Appl. No. 17/597,673 mailed Jun. 4, 2025.
Issue Notification for U.S. Appl. No. 17/625,941 mailed Feb. 25, 2026.
Issue Notification for U.S. Appl. No. 17/646,771 mailed Mar. 19, 2025.
Issue Notification for U.S. Appl. No. 17/653,137 mailed Feb. 4, 2025.
Issue Notification for U.S. Appl. No. 17/653,314 mailed Feb. 11, 2026.
Issue Notification for U.S. Appl. No. 17/653,920 mailed Oct. 22, 2025.
Issue Notification for U.S. Appl. No. 17/661,090 mailed Feb. 5, 2025.
Issue Notification for U.S. Appl. No. 17/663,330 mailed Feb. 26, 2025.
Issue Notification for U.S. Appl. No. 17/749,340 mailed May 28, 2025.
Issue Notification for U.S. Appl. No. 17/755,236 mailed Oct. 29, 2025.
Issue Notification for U.S. Appl. No. 17/758,316 mailed Jun. 25, 2025.
Issue Notification for U.S. Appl. No. 17/808,354 mailed Mar. 4, 2026.
Issue Notification for U.S. Appl. No. 17/878,268 mailed Feb. 4, 2026.
Issue Notification for U.S. Appl. No. 17/907,125 mailed Dec. 30, 2025.

(56) References Cited

OTHER PUBLICATIONS

Issue Notification for U.S. Appl. No. 17/912,147 mailed Mar. 18, 2026.
Issue Notification for U.S. Appl. No. 17/996,064 mailed Nov. 5, 2025.
Issue Notification for U.S. Appl. No. 17/996,155 mailed Oct. 8, 2025.
Issue Notification for U.S. Appl. No. 17/996,253 mailed Oct. 29, 2025.
Issue Notification for U.S. Appl. No. 17/996,468 mailed Nov. 26, 2025.
Issue Notification for U.S. Appl. No. 18/007,105 mailed Oct. 1, 2025.
Issue Notification for U.S. Appl. No. 18/044,413 mailed Dec. 30, 2025.
Issue Notification for U.S. Appl. No. 18/134,857 mailed May 28, 2025.
Issue Notification for U.S. Appl. No. 18/140,751 mailed Feb. 12, 2025.
Issue Notification for U.S. Appl. No. 18/260,122 mailed Nov. 12, 2025.
Issue Notification for U.S. Appl. No. 18/415,080 mailed Apr. 9, 2025.
Issue Notification for U.S. Appl. No. 18/426,795 mailed Feb. 19, 2025.
Issue Notification for U.S. Appl. No. 18/584,002 mailed Apr. 16, 2025.
Non-Final Office Action for U.S. Appl. No. 16/433,773 mailed Feb. 28, 2025.
Non-Final Office Action for U.S. Appl. No. 16/452,258 mailed Sep. 24, 2025.
Non-Final Office Action for U.S. Appl. No. 17/051,600 mailed Feb. 28, 2025.
Non-Final Office Action for U.S. Appl. No. 17/378,015 mailed Dec. 12, 2025.
Non-Final Office Action for U.S. Appl. No. 17/394,055 mailed Mar. 13, 2025.
Non-Final Office Action for U.S. Appl. No. 17/394,055 mailed Mar. 19, 2025.
Non-Final Office Action for U.S. Appl. No. 17/446,256 mailed Dec. 2, 2025.
Non-Final Office Action for U.S. Appl. No. 17/446,654 mailed May 1, 2025.
Non-Final Office Action for U.S. Appl. No. 17/451,354 mailed Mar. 19, 2025.
Non-Final Office Action for U.S. Appl. No. 17/595,747 mailed Jun. 12, 2025.
Non-Final Office Action for U.S. Appl. No. 17/628,411 mailed Dec. 22, 2025.
Non-Final Office Action for U.S. Appl. No. 17/631,619 mailed Mar. 19, 2025.
Non-Final Office Action for U.S. Appl. No. 17/635,866 mailed Jul. 29, 2025.
Non-Final Office Action for U.S. Appl. No. 17/645,821 mailed Mar. 31, 2025.
Non-Final Office Action for U.S. Appl. No. 17/653,137 mailed Jan. 28, 2025.
Non-Final Office Action for U.S. Appl. No. 17/653,314 mailed May 8, 2025.
Non-Final Office Action for U.S. Appl. No. 17/655,464 mailed Mar. 20, 2025.
Non-Final Office Action for U.S. Appl. No. 17/664,487 mailed May 19, 2025.
Non-Final Office Action for U.S. Appl. No. 17/754,736 mailed Mar. 31, 2025.
Non-Final Office Action for U.S. Appl. No. 17/756,201 mailed Apr. 24, 2025.
Non-Final Office Action for U.S. Appl. No. 17/757,311 mailed Sep. 2, 2025.
Non-Final Office Action for U.S. Appl. No. 17/758,152 mailed Apr. 8, 2025.
Non-Final Office Action for U.S. Appl. No. 17/759,587 mailed Jan. 26, 2026.
Non-Final Office Action for U.S. Appl. No. 17/759,697 mailed Sep. 17, 2025.
Non-Final Office Action for U.S. Appl. No. 17/809,083 mailed Apr. 2, 2025.
Non-Final Office Action for U.S. Appl. No. 17/809,083 mailed Mar. 7, 2025.
Non-Final Office Action for U.S. Appl. No. 17/878,268 mailed Mar. 17, 2025.
Non-Final Office Action for U.S. Appl. No. 17/912,147 mailed May 29, 2025.
Non-Final Office Action for U.S. Appl. No. 17/929,887 mailed Jun. 25, 2025.
Non-Final Office Action for U.S. Appl. No. 17/930,238 mailed Jun. 30, 2025.
Non-Final Office Action for U.S. Appl. No. 17/933,590 mailed Jul. 29, 2025.
Non-Final Office Action for U.S. Appl. No. 17/996,064 mailed Mar. 6, 2025.
Non-Final Office Action for U.S. Appl. No. 17/996,556 mailed Dec. 22, 2025.
Non-Final Office Action for U.S. Appl. No. 18/003,029 mailed Apr. 18, 2025.
Non-Final Office Action for U.S. Appl. No. 18/006,807 mailed May 29, 2025.
Non-Final Office Action for U.S. Appl. No. 18/034,902 mailed Mar. 20, 2026.
Non-Final Office Action for U.S. Appl. No. 18/042,842 mailed May 22, 2025.
Non-Final Office Action for U.S. Appl. No. 18/043,618 mailed May 19, 2025.
Non-Final Office Action for U.S. Appl. No. 18/043,807 mailed Feb. 10, 2026.
Non-Final Office Action for U.S. Appl. No. 18/115,444 mailed Oct. 22, 2025.
Non-Final Office Action for U.S. Appl. No. 18/139,523 mailed Nov. 19, 2025.
Non-Final Office Action for U.S. Appl. No. 18/150,360 mailed Nov. 5, 2025.
Non-Final Office Action for U.S. Appl. No. 18/164,800 mailed Apr. 25, 2025.
Non-Final Office Action for U.S. Appl. No. 18/246,121 mailed Jan. 22, 2026.
Non-Final Office Action for U.S. Appl. No. 18/247,986 mailed Jun. 4, 2025.
Non-Final Office Action for U.S. Appl. No. 18/249,577 mailed Nov. 17, 2025.
Non-Final Office Action for U.S. Appl. No. 18/254,638 mailed Nov. 17, 2025.
Non-Final Office Action for U.S. Appl. No. 18/259,626 mailed Jan. 30, 2026.
Non-Final Office Action for U.S. Appl. No. 18/259,626 mailed Jul. 11, 2025.
Non-Final Office Action for U.S. Appl. No. 18/260,394, filed Jan. 13, 2026.
Non-Final Office Action for U.S. Appl. No. 18/263,800 mailed Feb. 5, 2026.
Non-Final Office Action for U.S. Appl. No. 18/264,004 mailed May 15, 2025.
Non-Final Office Action for U.S. Appl. No. 18/264,278 mailed Nov. 10, 2025.
Non-Final Office Action for U.S. Appl. No. 18/265,736 mailed Jul. 1, 2025.
Non-Final Office Action for U.S. Appl. No. 18/376,274 mailed Mar. 9, 2026.
Non-Final Office Action for U.S. Appl. No. 18/548,152 mailed Sep. 16, 2025.
Non-Final Office Action for U.S. Appl. No. 18/549,387 mailed Mar. 4, 2026.

(56) References Cited

OTHER PUBLICATIONS

Non-Final Office Action for U.S. Appl. No. 18/551,492 mailed Mar. 19, 2026.
Non-Final Office Action for U.S. Appl. No. 18/553,625 mailed Oct. 2, 2025.
Non-Final Office Action for U.S. Appl. No. 18/556,945 mailed Dec. 19, 2025.
Non-Final Office Action for U.S. Appl. No. 18/562,626 mailed Feb. 11, 2026.
Non-Final Office Action for U.S. Appl. No. 18/563,672 mailed Feb. 12, 2026.
Non-Final Office Action for U.S. Appl. No. 18/662,216 mailed Mar. 9, 2026.
Non-Final Office Action for U.S. Appl. No. 18/682,006 mailed Mar. 4, 2026.
Non-Final Office Action for U.S. Appl. No. 18/689,532 mailed Mar. 19, 2026.
Non-Final Office Action for U.S. Appl. No. 18/690,392 mailed Feb. 9, 2026.
Non-Final Office Action for U.S. Appl. No. 18/694,090 mailed Mar. 17, 2026.
Non-Final Office Action for U.S. Appl. No. 18/757,964 mailed Aug. 20, 2025.
Non-Final Office Action for U.S. Appl. No. 29/892,478 mailed Mar. 12, 2026.
Notice of Allowance for U.S. Appl. No. 16/433,773 mailed Oct. 10, 2025.
Notice of Allowance for U.S. Appl. No. 16/904,868 mailed Jan. 21, 2025.
Notice of Allowance for U.S. Appl. No. 17/051,399 mailed Nov. 17, 2025.
Notice of Allowance for U.S. Appl. No. 17/051,600 mailed Jan. 5, 2026.
Notice of Allowance for U.S. Appl. No. 17/394,055 mailed Mar. 20, 2026.
Notice of Allowance for U.S. Appl. No. 17/444,792 mailed Mar. 28, 2025.
Notice of Allowance for U.S. Appl. No. 17/451,345 mailed Jun. 24, 2025.
Notice of Allowance for U.S. Appl. No. 17/451,354 mailed Nov. 18, 2025.
Notice of Allowance for U.S. Appl. No. 17/596,629 mailed Jan. 29, 2025.
Notice of Allowance for U.S. Appl. No. 17/596,629 mailed May 27, 2025.
Notice of Allowance for U.S. Appl. No. 17/597,673 mailed Feb. 26, 2025.
Notice of Allowance for U.S. Appl. No. 17/625,887 mailed Mar. 3, 2026.
Notice of Allowance for U.S. Appl. No. 17/625,941 mailed Nov. 13, 2025.
Notice of Allowance for U.S. Appl. No. 17/635,866 mailed Mar. 2, 2026.
Notice of Allowance for U.S. Appl. No. 17/645,821 mailed Nov. 24, 2025.
Notice of Allowance for U.S. Appl. No. 17/653,137 mailed Oct. 22, 2025.
Notice of Allowance for U.S. Appl. No. 17/653,314 mailed Oct. 20, 2025.
Notice of Allowance for U.S. Appl. No. 17/653,920 mailed Jul. 9, 2025.
Notice of Allowance for U.S. Appl. No. 17/749,340 mailed Feb. 14, 2025.
Notice of Allowance for U.S. Appl. No. 17/754,736 mailed Jan. 28, 2026.
Notice of Allowance for U.S. Appl. No. 17/755,236 mailed Jul. 17, 2025.
Notice of Allowance for U.S. Appl. No. 17/758,316 mailed Mar. 24, 2025.
Notice of Allowance for U.S. Appl. No. 17/759,697 mailed Jan. 30, 2026.
Notice of Allowance for U.S. Appl. No. 17/808,354 mailed Nov. 12, 2025.
Notice of Allowance for U.S. Appl. No. 17/878,268 mailed Oct. 15, 2025.
Notice of Allowance for U.S. Appl. No. 17/907,125 mailed Sep. 26, 2025.
Notice of Allowance for U.S. Appl. No. 17/912,147 mailed Dec. 3, 2025.
Notice of Allowance for U.S. Appl. No. 17/930,238 mailed Dec. 16, 2025.
Notice of Allowance for U.S. Appl. No. 17/996,064 mailed Jul. 29, 2025.
Notice of Allowance for U.S. Appl. No. 17/996,155 mailed Jun. 24, 2025.
Notice of Allowance for U.S. Appl. No. 17/996,155 mailed Mar. 11, 2025.
Notice of Allowance for U.S. Appl. No. 17/996,253 mailed Apr. 11, 2025.
Notice of Allowance for U.S. Appl. No. 17/996,253 mailed Jul. 11, 2025.
Notice of Allowance for U.S. Appl. No. 17/996,468 mailed Apr. 14, 2025.
Notice of Allowance for U.S. Appl. No. 17/996,468 mailed Jul. 15, 2025.
Notice of Allowance for U.S. Appl. No. 18/007,105 mailed Jun. 17, 2025.
Notice of Allowance for U.S. Appl. No. 18/041,109 mailed Mar. 25, 2026.
Notice of Allowance for U.S. Appl. No. 18/044,413 mailed Sep. 16, 2025.
Notice of Allowance for U.S. Appl. No. 18/134,857 mailed Feb. 20, 2025.
Notice of Allowance for U.S. Appl. No. 18/260,122 mailed Jul. 30, 2025.
Notice of Allowance for U.S. Appl. No. 18/264,004 mailed Jan. 30, 2026.
Notice of Allowance for U.S. Appl. No. 18/294,370 mailed Mar. 17, 2026.
Notice of Allowance for U.S. Appl. No. 18/610,523 mailed Mar. 4, 2026.
Restriction Requirement for U.S. Appl. No. 17/625,887 mailed Sep. 2, 2025.
Restriction Requirement for U.S. Appl. No. 17/755,236 mailed Apr. 24, 2025.
Restriction Requirement for U.S. Appl. No. 17/929,887 mailed Mar. 10, 2025.
Restriction Requirement for U.S. Appl. No. 17/930,238 mailed Apr. 17, 2025.
Restriction Requirement for U.S. Appl. No. 17/996,556 mailed Aug. 11, 2025.
Restriction Requirement for U.S. Appl. No. 18/034,902 mailed Nov. 6, 2025.
Restriction Requirement for U.S. Appl. No. 18/041,109 mailed Jun. 4, 2025.
Restriction Requirement for U.S. Appl. No. 18/041,109 mailed Oct. 23, 2025.
Restriction Requirement for U.S. Appl. No. 18/150,360 mailed May 19, 2025.
Restriction Requirement for U.S. Appl. No. 18/246,121 mailed Jul. 25, 2025.
Restriction Requirement for U.S. Appl. No. 18/249,577 mailed Aug. 25, 2025.
Restriction Requirement for U.S. Appl. No. 18/254,638 mailed Jul. 21, 2025.
Restriction Requirement for U.S. Appl. No. 18/260,394 mailed Jul. 25, 2025.
Restriction Requirement for U.S. Appl. No. 18/294,370 mailed Nov. 26, 2025.
Restriction Requirement for U.S. Appl. No. 18/294,403 mailed Jan. 27, 2026.

(56) References Cited

OTHER PUBLICATIONS

Restriction Requirement for U.S. Appl. No. 18/335,579 mailed Nov. 26, 2025.
Restriction Requirement for U.S. Appl. No. 18/373,424 mailed Nov. 14, 2025.
Restriction Requirement for U.S. Appl. No. 18/376,274 mailed Dec. 10, 2025.
Restriction Requirement for U.S. Appl. No. 18/549,387 mailed Dec. 9, 2025.
Restriction Requirement for U.S. Appl. No. 18/551,492 mailed Nov. 10, 2025.
Restriction Requirement for U.S. Appl. No. 18/558,502 mailed Jan. 29, 2026.
Restriction Requirement for U.S. Appl. No. 18/569,711 mailed Jan. 6, 2026.
Restriction Requirement for U.S. Appl. No. 18/569,778 mailed Jan. 15, 2026.
Restriction Requirement for U.S. Appl. No. 18/662,216 mailed Nov. 26, 2025.
Restriction Requirement for U.S. Appl. No. 18/687,117 mailed Mar. 26, 2026.
Restriction Requirement for U.S. Appl. No. 19/237,638 mailed Dec. 18, 2025.
Supplemental Notice of Allowance for U.S. Appl. No. 17/597,673 mailed Apr. 10, 2025.
U.S. Appl. No. 17/051,399, filed Oct. 28, 2020.
U.S. Appl. No. 17/596,629, filed Dec. 15, 2021.
U.S. Appl. No. 17/625,941, filed Jan. 10, 2022.
U.S. Appl. No. 18/034,902, filed May 2, 2023.
U.S. Appl. No. 19/038,774, filed Jan. 28, 2025.
U.S. Appl. No. 19/039,165, filed Jan. 28, 2025.
U.S. Appl. No. 19/046,047, filed Feb. 5, 2025.
U.S. Appl. No. 19/047,728, filed Feb. 7, 2025.
U.S. Appl. No. 19/048,004, filed Feb. 7, 2025.
U.S. Appl. No. 19/049,501, filed Feb. 10, 2025.
U.S. Appl. No. 19/049,783, filed Feb. 10, 2025.
U.S. Appl. No. 19/058,726, filed Feb. 20, 2025.
U.S. Appl. No. 19/069,480, filed Mar. 4, 2025.
U.S. Appl. No. 19/078,602, filed Mar. 13, 2025.
U.S. Appl. No. 19/092,262, filed Mar. 27, 2025.
U.S. Appl. No. 19/103,165, filed Feb. 11, 2025.
U.S. Appl. No. 19/110,938, filed Mar. 12, 2025.
U.S. Appl. No. 19/111,921, filed Mar. 14, 2025.
U.S. Appl. No. 19/127,234, filed May 5, 2025.
U.S. Appl. No. 19/171,983, filed Apr. 7, 2025.
U.S. Appl. No. 19/179,540, filed Apr. 15, 2025.
U.S. Appl. No. 19/202,862, filed May 8, 2025.
U.S. Appl. No. 19/207,699, filed May 14, 2025.
U.S. Appl. No. 19/215,723, filed May 22, 2025.
U.S. Appl. No. 19/237,368, filed Jun. 13, 2025.
U.S. Appl. No. 19/240,380, filed Jun. 17, 2025.
U.S. Appl. No. 19/329,723, filed Sep. 16, 2025.
U.S. Appl. No. 19/337,217, filed Sep. 23, 2025.
U.S. Appl. No. 19/353,151, filed Oct. 8, 2025.
U.S. Appl. No. 19/356,506, filed Oct. 13, 2025.
U.S. Appl. No. 19/358,647, filed Oct. 15, 2025.
U.S. Appl. No. 19/370,361, filed Oct. 27, 2025.
U.S. Appl. No. 19/418,150, filed Dec. 12, 2025.
U.S. Appl. No. 19/443,729, filed Jan. 8, 2026.
U.S. Appl. No. 19/447,347, filed Jan. 13, 2026.
U.S. Appl. No. 19/451,614, filed Jan. 16, 2026.
U.S. Appl. No. 19/491,481, filed Dec. 9, 2025.
U.S. Appl. No. 19/494,631, filed Dec. 18, 2025.
U.S. Appl. No. 19/510,850, filed Feb. 12, 2026.
U.S. Appl. No. 19/513,755, filed Feb. 24, 2026.
U.S. Appl. No. 19/513,838, filed Feb. 24, 2026.
U.S. Appl. No. 19/514,100, filed Feb. 25, 2026.
U.S. Appl. No. 19/534,156, filed Feb. 9, 2026.
U.S. Appl. No. 19/535,649, filed Feb. 10, 2026.
U.S. Appl. No. 19/539,961, filed Feb. 13, 2026.
U.S. Appl. No. 19/541,655, filed Feb. 17, 2026.
U.S. Appl. No. 19/544,501, filed Feb. 19, 2026.
U.S. Appl. No. 19/554,125, filed Mar. 2, 2026.
U.S. Appl. No. 63/181,709, filed Apr. 29, 2021.

* cited by examiner

FLUID COLLECTION DEVICES, FLUID COLLECTION SYSTEMS INCLUDING THE SAME, AND METHODS OF USING THE SAME

CROSS-REFERENCE TO RELATED APPLICATIONS

This application is a U.S. Nationalization of PCT International Application No. PCT/US2020/033122 filed on May 15, 2020, which claims priority to U.S. Provisional Application No. 62/853,279 filed on May 28, 2019, the disclosure which is incorporated, in its entirety, by this reference.

BACKGROUND

An individual may have limited or impaired mobility such that typical urination processes are challenging or impossible. For example, the individual may experience or have a disability that impairs mobility. The individual may have restricted travel conditions such as those experienced by pilots, drivers, and workers in hazardous areas. Additionally, sometimes urine collection is needed for monitoring purposes or clinical testing.

Urinary catheters, such as a Foley catheter, may be used to address some of these circumstances, such as incontinence. However, urinary catheters may be uncomfortable, painful, and may lead to complications, such as infections. In another embodiment, bed pans, which are receptacles used for the toileting of bedridden patients, such as those in a health care facility, are sometimes used to address some of these circumstances. However, bed pans may be prone to discomfort, spills, and other hygiene issues.

When the individual is a male, condom-style catheters may be used to address some of the circumstances disclosed above. Condom-style catheters may include a fluid impermeable shell defining a chamber and an opening. The opening and the chamber may be configured to have the male penis inserted through the hole such that the urethral opening of the individual is disposed in the chamber.

SUMMARY

In an embodiment, a fluid collection device is disclosed. The fluid collection device includes a fluid impermeable barrier defining a chamber, an opening, and an outlet. The fluid collection device also includes a fluid permeable membrane extending across the opening. The fluid collection device further includes a fluid receiving portion including a portion of the fluid impermeable barrier that at least partially defines the opening and an longitudinal portion extending from the fluid receiving portion. The fluid collection device exhibits a maximum length measured from a distal tip of the longitudinal portion to an opposing portion of the fluid receiving portion. The fluid receiving portion exhibits a first maximum width measured perpendicular to the maximum length, and the longitudinal portion exhibits a second maximum width measured parallel to the first maximum width. The first maximum width is greater than the second maximum width.

In an embodiment, a fluid collection system is disclosed. The fluid collection system includes a fluid collection device. The fluid collection device includes a fluid impermeable barrier defining a chamber, an opening, and an outlet. The fluid collection device also includes a fluid permeable membrane extending across the opening. The fluid collection device further includes a fluid receiving portion including a portion of the fluid impermeable barrier that at least partially defines the opening and an longitudinal portion extending from the fluid receiving portion. The fluid collection device exhibits a maximum length measured from a distal tip of the longitudinal portion to an opposing portion of the fluid receiving portion. The fluid receiving portion exhibits a first maximum width measured perpendicular to the maximum length, and the longitudinal portion exhibits a second maximum width measured parallel to the first maximum width. The first maximum width is greater than the second maximum width. a fluid collection container in fluid communication with and positioned downstream from the fluid collection device. The fluid collection system also includes a fluid collection container in fluid communication with and positioned downstream from the fluid collection device. The fluid collection system further includes a suction source in fluid communication with the fluid collection device and the fluid collection container. The fluid collection system additionally includes at least one tube that allows the fluid collection device to be in fluid communication with the fluid collection container and the suction source.

In an embodiment, a method is disclosed. The method includes providing a fluid collection device. The fluid collection device includes a fluid impermeable barrier defining a chamber, an opening, and an outlet. The fluid collection device also includes a fluid permeable membrane extending across the opening. The fluid collection device further includes a fluid receiving portion including a portion of the fluid impermeable barrier that at least partially defines the opening and an longitudinal portion extending from the fluid receiving portion. The fluid collection device exhibits a maximum length measured from a distal tip of the longitudinal portion to an opposing portion of the fluid receiving portion. The fluid receiving portion exhibits a first maximum width measured perpendicular to the maximum length, and the longitudinal portion exhibits a second maximum width measured parallel to the first maximum width. The first maximum width is greater than the second maximum width. The method also includes positioning the opening of the fluid collection device adjacent to a urethral opening of an individual. The method further includes positioning the longitudinal portion against a perineum and/or upper thighs of the individual.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

DETAILED DESCRIPTION

Figure 1B:
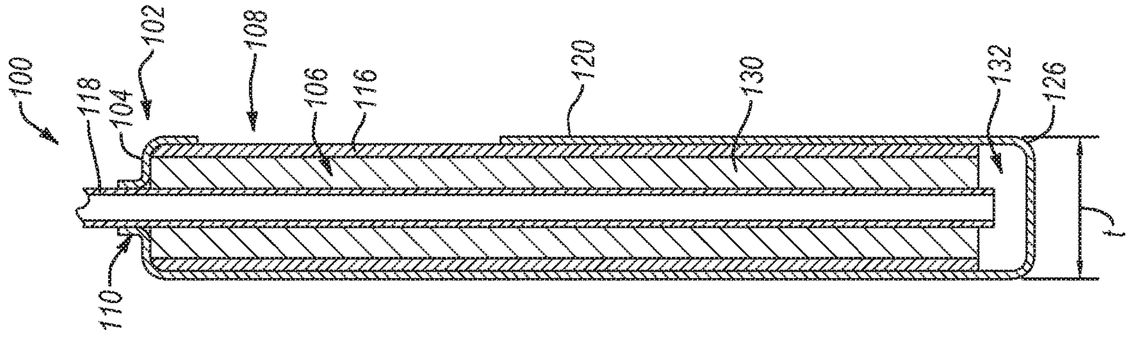
FIG. 1B is a cross-sectional view of the fluid collection system, according to an embodiment.

Urinary collection devices, urinary collection systems including the same, and methods of using the same are disclosed herein. An example urinary collection device includes a fluid impermeable barrier defining a chamber, an opening, and an outlet. The opening and the outlet enable fluid to enter and leave the chamber, respectively. The urinary collection device also includes a fluid permeable membrane extending across the opening. The fluid permeable membrane may restrict or prevent a penis from entering the chamber. The urinary collection device includes a fluid receiving portion that includes the portions of the fluid impermeable barrier that defines the opening. The fluid receiving portion is configured to be positioned such that the opening is disposed adjacent to a urethral opening of the individual (e.g., a buried penis). The urinary collection device also includes a longitudinal portion (e.g., elongated portion) extending from the fluid receiving portion. The longitudinal portion is configured to be positioned adjacent to or near the perineum of the individual (e.g., positioned between the thighs of the individual). The urinary collection device exhibits a maximum length measured from a distal tip of the longitudinal portion to an opposing portion of the fluid receiving portion.

To facilitate their respective functions, the fluid receiving portion and the longitudinal portion exhibit different widths that are measured perpendicularly relative to the maximum length of the urinary collection device. For example, the fluid receiving portion exhibits a width that is generally greater than the width of the longitudinal portion. For instance, the fluid receiving portion exhibits a first maximum width and the longitudinal portion exhibits a second maximum width, and wherein the first maximum width is greater than the second maximum width. However, it is noted that portions of the fluid receiving portion, such as at or near a distal portion of the fluid receiving portion, may exhibit a width that is smaller than the longitudinal portion. The relatively larger width of the fluid receiving portion facilitates the opening receiving substantially all of the fluid (e.g., urine, sweat, and other bodily fluids) that is discharged from or around the urethral opening of the individual. The relatively smaller width of the longitudinal portion allows the longitudinal portion to be more comfortably positioned at or near the perineum of the individual.

In an embodiment, the fluid receiving portion and the longitudinal portion may be distinguishable from each other by their respective widths. In an example, the width of the fluid collection device changes abruptly or substantially abruptly between the fluid receiving portion and the longitudinal portion. In an example, a rate that the widths of the fluid collection device changes between the fluid receiving portion and the longitudinal portion changes. In such an example, for instance, the width of the fluid receiving portion may be changing at or near an intersection of the fluid receiving portion (e.g., decreasing with increasing proximity to the intersection) while the width of the longitudinal portion may be substantially constant at or near the intersection of the fluid receiving portion. In an embodiment, the fluid receiving portion and the longitudinal portion are distinguishable from each other because the fluid receiving portion and the longitudinal portion exhibit different shapes. For example, the fluid receiving portion may exhibit a generally triangular shape (FIG. 1A), a generally circular shape (FIG. 3), a generally rectangular shape, or another suitable shape while the longitudinal portion exhibits a longitudinal shape (e.g., an oblong shape) that extends from the fluid receiving portion. In an embodiment, the fluid receiving portion and the longitudinal portion are distinguishable because the fluid receiving portion exhibits a size (e.g., width) that is too large to be comfortably positioned at and/or near the perineum of the individual while the longitudinal portion exhibits a size that allows the longitudinal portion to be comfortably positioned at and/or near the perineum. In an embodiment, the fluid receiving portion and the longitudinal portion are distinguishable because the fluid receiving portion defines substantially all (e.g., all) of the opening while the longitudinal portion does not.

In an embodiment, the fluid collection devices disclosed herein are configured to receive urine from a buried penis of a male individual. For example, as previously discussed, it may be difficult or impossible to use condom-style catheters with a buried penis. However, the fluid receiving portion of the fluid collection device may be positioned adjacent to the buried penis and the large width of the fluid receiving portion allows the opening to receive substantially all, if not all, of the bodily fluids discharged from or around the buried penis. For instance, the large width of the fluid receiving portion may allow the opening to receive urine even when the buried penis is angled relative to the fluid receiving portion and the large surface area of the opening (that is partially caused by the large width of the fluid receiving portion) allows the fluid receiving portion to receive urine that was not initially absorbed by the fluid permeable membrane. However, it is noted that the fluid collection devices disclosed herein may be used in connection with female urethras or non-buried penises.

Figure 1A:
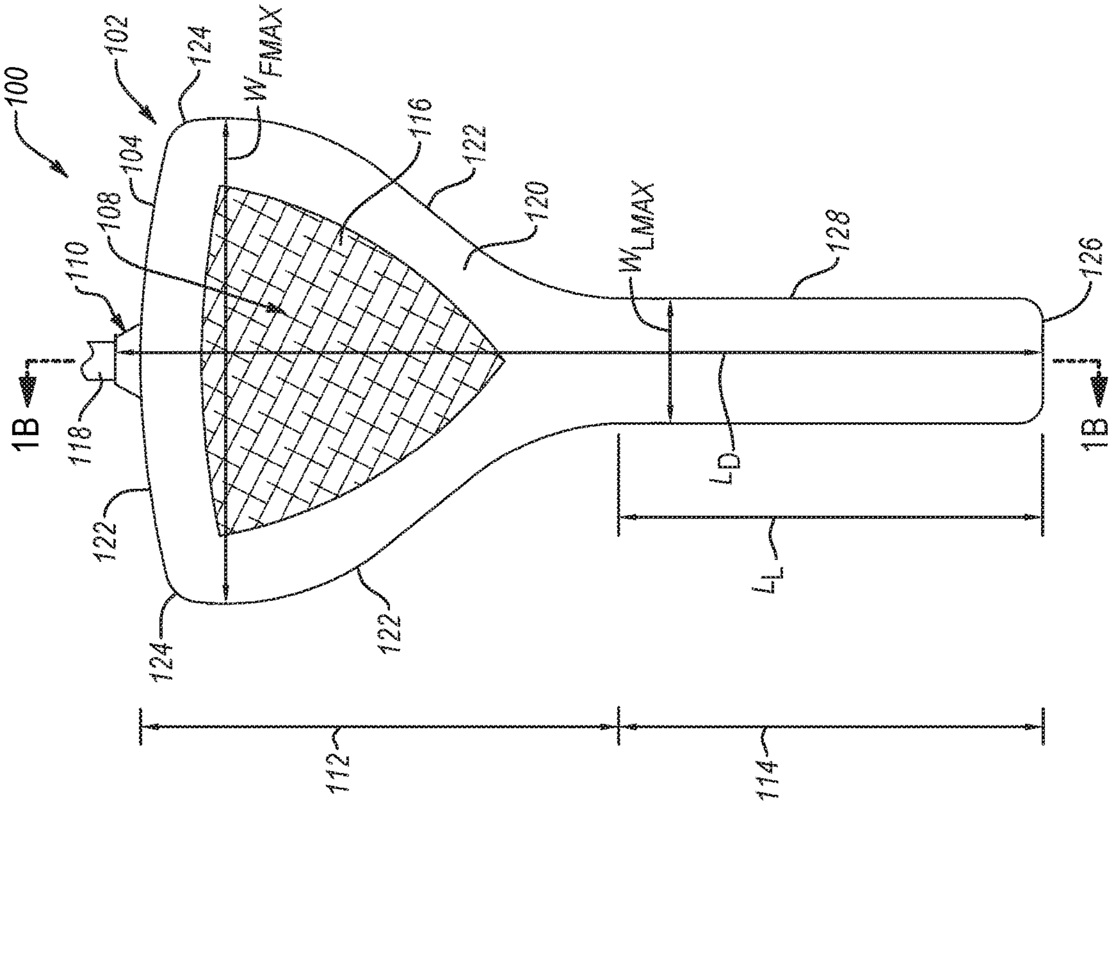
FIG. 1A is a top plan view of a portion of a fluid collection system that includes a fluid collection device, according to an embodiment.

FIG. 1A is a top plan view of a portion of a fluid collection system 100 that includes a fluid collection device 102, according to an embodiment. The fluid collection device 102 includes a fluid impermeable barrier 104. The fluid impermeable barrier 104 defines a chamber 106 (shown in FIG. 1B), an opening 108, and an outlet 110. The fluid collection device 102 also includes a fluid permeable membrane 116 extending over the opening 108. The fluid permeable membrane 116 may allow fluids (e.g., urine) to enter the chamber 106 while substantially preventing a urethral opening (e.g., penis) from enter the chamber 106. The fluid collection device 102 further includes a fluid receiving portion 112 that is configured to be positioned adjacent to the urethral opening (e.g., a buried penis) and an longitudinal portion 114 that is configured to be positioned at and/or near a perineum of the individual. The fluid collection system 100 also includes at least one tube 118 in fluid communication with the chamber 106 via the outlet 110. For example, the tube 118 may be positioned in the outlet 110 such that a portion of the tube 118 is disposed in the chamber 106. Thus, the tube 118 may remove fluid from the chamber 106, as will be discussed in more detail with regards to FIG. 5.

The fluid impermeable barrier 104 may include any fluid (e.g., urine) impermeable material. For example, the fluid impermeable barrier 104 may include a fluid impermeable polymer (e.g., silicone, polypropylene, polyethylene, polyethylene terephthalate, a polycarbonate, other elastomeric material, etc.), a metal film, natural rubber, another suitable material, or combinations thereof. As such, the fluid impermeable barrier 104 substantially prevents the fluids from passing through the fluid impermeable barrier 104. In an example, the fluid impermeable barrier 104 may be air permeable and fluid impermeable. In such an example, the fluid impermeable barrier 104 may be formed of a hydrophobic material that defines a plurality of pores. At least one or more portions of at least an outer surface of the fluid impermeable barrier 104 may be formed from a soft and/or smooth material, thereby reducing chaffing. During use, a portion of the outer surface of the fluid impermeable barrier 104 may contact the wearer.

In an embodiment, forming the fluid impermeable barrier 104 from silicone and/or another elastomeric material allows the fluid impermeable barrier 104 to be bendable. Allowing the fluid impermeable barrier 104 to be bendable may make the fluid collection device 102 more comfortable to use than if the fluid impermeable barrier 104 was formed from another material. Further, as previously discussed, the fluid collection device 102 is configured to be used with a buried penis. Individuals with buried penises are often overweight and a bendable fluid impermeable barrier 104 may allow the fluid impermeable barrier 104 to bend around and/or conform to bulges caused by body fat. Bending the fluid impermeable barrier 104 around and/or conforming to the bulges caused by the body fat may inhibit fluids from avoiding the opening 108 and flowing around the fluid impermeable barrier 104.

The fluid impermeable barrier 104, in part, defines and forms the fluid receiving portion 112 and the longitudinal portion 114. For example, the fluid impermeable barrier 104 may be formed to exhibit the size and shape of the fluid receiving portion 112 and the longitudinal portion 114. However, it is noted that the other components of the fluid collection device 102 also define and form the fluid receiving portion 112 and the longitudinal portion 114. For example, the components of the fluid collection device 102 that are disposed in the chamber 106 (e.g., the fluid permeable membrane 116 and the fluid permeable support 130) may also support the fluid impermeable barrier 104 such that the fluid impermeable barrier 104 forms the shape of the fluid receiving portion 112 and the longitudinal portion 114.

As previously discussed, the fluid collection device 102 exhibits a length $L_D$ extending from a distal tip 126 of the longitudinal portion 114 to an opposing portion of the fluid receiving portion 112. In the illustrated embodiment, the opposing portion of the fluid receiving portion 112 is the outlet 110, though there is no requirement that the outlet 110 is positioned at the opposing portion of the fluid receiving portion 112. The length $L_D$ of the fluid collection device 102 may be selected based on at least the size of the individual (e.g., the size of the individual's groin), the type of urethral opening that the fluid collection device 102 is positioned adjacent to (e.g., a buried penis may require a larger fluid receiving portion 112 than a female urethral opening due to at least the various angles that the buried penis may emit urine), and the method used to attach the longitudinal portion 114 to the individual (e.g., using an adhesive may allow for a smaller longitudinal portion 114). In other words, the length $L_D$ of the fluid collection device 102 may vary from one embodiment to the next. However, generally, the length $L_D$ of the fluid collection device 102 may be greater than about 10 cm, greater than about 12 cm, greater than about 14 cm, greater than about 16 cm, greater than about 18 cm, greater than about 20 cm, greater than about 22 cm, greater than about 24 cm, greater than about 26 cm, greater than about 28 cm, greater than about 30 cm, greater than about 33.5 cm, greater than about 35 cm, greater than about 37.5 cm, greater than about 40 cm, greater than about 45 cm, or in ranges of about 10 cm to about 14 cm, about 12 cm to about 16 cm, about 14 cm to about 18 cm, about 16 cm to about 20 cm, about 18 cm to about 22 cm, about 20 cm to about 24 cm, about 22 cm to about 26 cm, about 24 cm to about 28 cm, about 26 cm to about 30 cm, about 28 cm to about 32.5 cm, about 30 cm to about 35 cm, about 32.5 cm to about 37.5 cm, about 35 cm to about 40 cm, or about 37.5 cm to about 45 cm. The length $L_D$ of the fluid collection device 102 may be selected based on the size of the individual, the size of the penis of the individual, the length of the perineum of the individual, and the shape of the opening 108. For example, individuals that are larger (e.g., have larger penises, longer perineums, etc.) may require or be able to accommodate a fluid collection device 102 exhibit a larger length $L_D$ (e.g., greater than about 15 cm, greater than about 20 cm, or greater than about cm) than smaller patients. Further increasing the length $L_D$ of the fluid collection device 102 may increase the amount of fluids received by the fluid collection device 100 and the amount of fluids that may be held within the chamber 106. However, some individuals (e.g., smaller individuals) may be unable to use a fluid collection device 102 exhibiting longer lengths $L_D$.

As previously discussed, the fluid receiving portion 112 is configured to be positioned adjacent to a urethral opening of an individual, such as a buried penis, and to receive fluids from the urethral opening. As such, the fluid receiving portion 112 at least partially defines the opening 108. For example, the fluid receiving portion 112 defines all of or a substantial majority of the opening 108. Since the fluid receiving portion 112 defines the opening 108, positioning the fluid receiving portion 112 adjacent to the urethral opening of the individual also positions the opening 108 adjacent to the urethral opening. Positioning the opening 108 adjacent to the urethral opening increases the percentage of fluid that is discharged from the urethral opening that both reaches the opening 108 (e.g., contact the fluid permeable membrane 116) and enters the chamber 106.

The fluid receiving portion 112 exhibits a shape that allows the fluid receiving portion 112 to be positioned adjacent to the urethral opening. Generally, the front face 120 of the fluid receiving portion 112 exhibits a shape that allows the fluid receiving portion 112 to abut the urethral opening. For example, the front face 120 may exhibit a generally planar topography or may have a concave curved topography which allows the front face 120 to conform to the groin of the individual since the groin is generally planar or has a convex curvature.

The fluid receiving portion 112 may also exhibit a shape that is configured to increase the size of the opening 108. For example, increasing the size of the fluid receiving portion 112 may allow the fluid receiving portion 112 to define a larger opening 108. The larger opening 108 allows the opening 108 to receive fluids that is emitted from a buried penis at different directions. Further, the larger opening 108 allows the opening 108 to receive fluid that would have otherwise leaked between the fluid impermeable barrier 104 and the skin of the individual. In an embodiment, the fluid receiving portion 112 may exhibit a generally triangular shape. The generally triangular shape may allow the fluid receiving portion 112 to correspond to the shape of the groin that surrounds the urethral opening since the groin exhibits a generally triangular shape, especially when the thighs of the individual contact each other (which is common for obese individuals). As such, the generally triangular shape of the fluid receiving portion 112 may allow the fluid receiving portion 112 to exhibit the maximum possible size without minimally uncomfortably pressing into the individual. As will be discussed in more detail below, the fluid receiving portion 112 may exhibit other suitable shapes.

When the fluid receiving portion 112 exhibits the generally triangular shape, the fluid receiving portion 112 may include three edges 122 and at least two vertices 124 (e.g., in some embodiments, the longitudinal portion 114 may extend from and obscure a vertex). In the illustrated embodiment, the edges 122 may be convexly curved which may at least one of cause the edges 122 to slightly press into the individual to position and secure the fluid receiving portion 112 to the groin or to conform to the groin of the individual when the edges of the groin are convex. The convex curvature of the edges 122 may also increase the volume of the chamber 106 which, in turn, increases the volume of fluid that may be held in the chamber 106 at any given time. However, it is noted that the edges 122 may be straight or convexly curved (e.g., convexly curved edges 122 may be used with extremely obese individuals). Generally, any exposed vertices 124 (e.g., any vertex that the longitudinal portion 114 does not extend from) may be rounded which may inhibit the vertices 124 from causing discomfort.

In an embodiment, as illustrated, the opening 108 exhibits a shape that corresponds to the shape of the fluid receiving portion 112 which allows the opening 108 to exhibit the largest possible size. However, it is noted that the opening 108 may exhibit a shape that is different than the shape of the fluid receiving portion 112. For example, the fluid receiving portion 112 may exhibit a generally triangular shape while the opening 108 may exhibit a generally circular shape. The generally circular shape of the opening 108 may allow the fluid receiving portion 112 to be positioned such that the distance from the urethral opening to the edge of the opening 108 is substantially constant since smaller distances from the urethral opening to the edge of the opening 108 are more likely to induce fluid leaks.

The fluid receiving portion 112 exhibits a width that is measured perpendicularly to the length $L_D$ of the fluid collection device 102. The fluid receiving portion 112 exhibits a maximum width $W_{Fmax}$. The maximum width $W_{FMax}$ of the fluid receiving portion 112 may be selected based on the size of the individual (e.g., the size of the individual's groin) and the type of urethral opening that the fluid collection device 102 is positioned adjacent to (e.g., a buried penis may require a larger fluid receiving portion 112 than a female urethral opening due to at least the various angles that the buried penis may emit urine). In other words, the maximum width $W_{FMax}$ of the fluid receiving portion 112 may be selected based on the application of the fluid collection device 102. The maximum width $W_{FMax}$ may be at least about 7.5 cm, at least about 10 cm, at least about 12 cm, at least about 14 cm, at least about 16 cm, at least about 18 cm, at least about 20 cm, at least about 22 cm, at least about 24 cm, at least about 26 cm, at least about 28 cm, at least about 30 cm, or in ranges of about 7.5 cm to about 12 cm, about 10 cm to about 14 cm, at least 12 cm to about 16 cm, about 14 cm to about 18 cm, about 16 cm to about 20 cm, about 18 cm to about 22 cm, about 20 cm to about 24 cm, about 22 cm to about 26 cm, about 24 cm to about 28 cm, or about 26 cm to about 30 cm. The maximum width $W_{FMax}$ may be selected based on the size of the individual and, more particularly, the space between the thighs of the patient. For example, the maximum width $W_{FMax}$ may be selected to be at or near the maximum width $W_{FMax}$ that an individual may accommodate since, generally, increasing the maximum width $W_{FMax}$ may increase the amount of fluids that are received by the fluid collection device 100. In the illustrated embodiment, the maximum width $W_{FMax}$ is spaced from the vertices 124 due to the convex shape of the edges 122. However, it is noted that the maximum width $W_{FMax}$ may be located at the vertices 124.

The fluid impermeable barrier 104 exhibits a thickness that is micrometer sized (e.g., about 100 μm to about 1000 μm) to a few millimeters (e.g., about 1 mm to about 5 mm). As such, the portion of the chamber 106 that form part of the fluid receiving portion 112 may exhibit maximum width (not shown, obscured) that is comparable to the maximum width $W_{FMax}$. For example, the portion of the chamber 106 that form part of the fluid receiving portion 112 may exhibit a maximum width that is at least about 7 cm, at least about 10 cm, at least about 12 cm, at least about 14 cm, at least about 16 cm, at least about 18 cm, at least about 20 cm, at least about 22 cm, at least about 24 cm, at least about 26 cm, at least about 28 cm, at least about 30 cm, or in ranges of about 7.5 cm to about 12 cm, about 10 cm to about 14 cm, at least 12 cm to about 16 cm, about 14 cm to about 18 cm, about 16 cm to about 20 cm, about 18 cm to about 22 cm, about 20 cm to about 24 cm, about 22 cm to about 26 cm, about 24 cm to about 28 cm, or about 26 cm to about 30 cm. As previously discussed, the maximum width of the chamber 106 may be selected based on the maximum width $W_{FMax}$. The maximum width of the chamber 106 that forms part of the fluid receiving portion 112 may be selected using the same factors as the maximum width $W_{FMax}$. The maximum width of the chamber 106 may also be selected based on the thickness of the fluid impermeable barrier 104 and the desired amount of fluid that may be held in the chamber 106.

As previously discussed, the fluid collection device 102 includes an longitudinal portion 114 that extends from the fluid receiving portion 112. For example, as illustrated, the longitudinal portion 114 extends from a vertex of the generally triangular shape of the fluid receiving portion 112. The longitudinal portion 114 is distinguishable from the fluid receiving portion 112 based on the widths thereof. For example, in the illustrated embodiment, the width of the fluid receiving portion 112 generally decreases from the maximum width $W_{FMax}$ to the longitudinal portion 114 while the thickness of the longitudinal portion 114 remains substantially constant from the intersection of the fluid receiving portion 112 and the longitudinal portion 114 along at least a portion of a length of the longitudinal portion 114.

The longitudinal portion 114 is configured to be positioned at and/or near the perineum of an individual. In other words, the longitudinal portion 114 is configured to be positioned between the thighs of the individual. Due to the limited space at and/or near the perineum of the individual, the width of the longitudinal portion 114 is generally less than the width of the fluid receiving portion 112. However, it is noted that the width of the longitudinal portion 114 may be greater than localized regions of the fluid receiving portion 112 (e.g., the width of the longitudinal portion 114 is greater than the width of the outlet 110 and the portions of the fluid receiving portion 112 about the outlet 110). The longitudinal portion 114 exhibits a maximum width $W_{LMax}$ that is about 1 cm to about 7.5 cm, such as in ranges of about 1 cm to about 2 cm, about 1.5 cm to about 2.5 cm, about 2 cm to about 3 cm, about 2.5 cm to about 3.5 cm, about 3 cm to about 4 cm, about 3.5 cm to about 4.5 cm, about 4 cm to about 5 cm, about 4.5 cm to about 5.5 cm, about 5 cm to about 6 cm, about 5.5 cm to about 6.5 cm, about 6 cm to about 7 cm, or about 6.5 cm to about 7.5 cm. The maximum width $W_{LMax}$ may be selected based on the required attachment force required to maintain the fluid receiving portion 112 adjacent to the urethral opening of the individual since, generally, increasing the width of the longitudinal portion 114 increases the attachment force. For example, strongly attaching the longitudinal portion 114 to the individual, such as with an adhesive, may allow the longitudinal portion 114 to exhibit a smaller maximum width $W_{LMax}$ than if the longitudinal portion 114 relies on friction from the perineum and/or thighs (e.g., interference fit) to hold the longitudinal portion 114 in place. Also, the maximum width $W_{LMax}$ may be selected based on the size of fluid receiving portion 112 since increasing the size of the fluid receiving portion 112 requires a larger attachment force to maintain the position of the fluid receiving portion 112. The maximum width $W_{LMax}$ may be selected based on the size of the perineum and/or the space between the thighs of the individual using the fluid collection device 100 since the longitudinal portion 114 may be at least partially positioned adjacent to the perineum and/or between the thighs.

As previously discussed, the fluid impermeable barrier 104 exhibits a thickness that is micrometer sized to a few millimeters. As such, the portion of the chamber 106 that form part of the longitudinal portion 114 exhibits maximum width (not shown, obscured) that is comparable to the maximum width $W_{LMax}$. For example, the portion of the chamber 106 that form part of the longitudinal portion 114 may exhibit a maximum width that is about 0.5 cm to about 7.5 cm, such as in ranges of about 1 cm to about 2 cm, about 1.5 cm to about 2.5 cm, about 2 cm to about 3 cm, about 2.5 cm to about 3.5 cm, about 3 cm to about 4 cm, about 3.5 cm to about 4.5 cm, about 4 cm to about 5 cm, about 4.5 cm to about 5.5 cm, about 5 cm to about 6 cm, about 5.5 cm to about 6.5 cm, about 6 cm to about 7 cm, or about 6.5 cm to about 7.5 cm. The maximum width of the chamber 106 that forms part of the longitudinal portion 114 may be selected using the same factors as the maximum width $W_{LMax}$. The maximum width of the chamber 106 may also be selected based on the thickness of the fluid impermeable barrier 104 and the desired amount of fluid that may be held in the chamber 106.

In the illustrated embodiment, the longitudinal portion 114 includes two edges 128 extending from the fluid receiving portion 112 and the width of the longitudinal portion 114 may be measured between the two edges 128. The two edges 128 are illustrated as being substantially straight such that the width of the longitudinal portion 114 remains constant or substantially constant. However, it is noted that the two edges 128 may be curved or exhibit another type of contour. In an example, the two edges 128 may be convexly curved to increase contact between the longitudinal portion 114 and the thighs of the individual to improve the attachment (e.g., interference fit) between the longitudinal portion 114 and the thighs. In an example, the two edges 128 may be concavely curved to better accommodate bulges of body fat thereby making the longitudinal portion 114 more comfortable. In an example, at least a portion of the two edges 128 may be tapered to better fit between the thighs of the individual.

The longitudinal portion 114 also exhibits a length $L_L$ extending between the distal tip 126 of the longitudinal portion 114 to the intersection between the fluid receiving portion 112 and the longitudinal portion 114. The length $L_L$ is measured perpendicularly to the length $L_D$ of the fluid collection device 102. The length $L_L$ may be at least about 5 cm, at least about 7.5 cm, at least about 10 cm, at least about 12 cm, at least about 14 cm, at least about 16 cm, at least about 18 cm, at least about 20 cm, at least about 22 cm, at least about 24 cm, at least about 26 cm, at least about 28 cm at least about 30 cm, or in ranges of about 5 cm to about 10 cm, about 7.5 cm to about 12 cm, 10 cm to about 14 cm, about 12 cm to about 16 cm, at least 14 cm to about 18 cm, about 16 cm to about 20, about 18 cm to about 22 cm, about 20 cm to about 24 cm, about 22 cm to about 26 cm, about 24 cm to about 28 cm, or about 26 cm to about 30 cm. Similar to the maximum width $W_{LMax}$, the length $L_L$ of the longitudinal portion 114 may be selected based on the required attachment force required to maintain the fluid receiving portion 112 adjacent to the urethral opening of the individual since, generally, increasing the width of the longitudinal portion 114 increases the attachment force. The length $L_L$ of the longitudinal portion 114 may be selected based on the size of the perineum since the longitudinal portion 114 may be at least partially positioned adjacent to the perineum.

FIG. 1B is a cross-sectional view of the fluid collection system 100, according to an embodiment. As shown in FIG. 1B, the fluid collection device 102 exhibits a substantially constant thickness t along substantially the entirety of the length $L_D$ of the fluid collection device 102. However, in other embodiments, the thickness t may vary along the length $L_D$. For example, as illustrated, the thickness t may be substantially constant except near the outlet 110, near the distal tip 126, and at the opening 108. The uniform thickness of the fluid collection device 102 may allow the fluid collection device 102 to be worn discretely. However, the thickness of the fluid collection device 102 may vary. In an example, thickness of the fluid receiving portion 112 may be selected to be larger than the thickness of the longitudinal portion 114 to increase the volume of fluid that may be stored in the chamber 106. In an example, the thickness of the fluid receiving portion 112 may be selected to be smaller than the thickness of the longitudinal portion 114 to further increase the ability of the fluid collection device 102 to be worn discretely.

As previously discussed, the fluid collection device 102 may include a fluid permeable membrane 116 disposed in the chamber 106. The fluid permeable membrane 116 may extend across at least a portion (e.g., all) of the opening 108. The fluid permeable membrane 116 may be configured to wick any fluid away from the opening 108 thereby allowing fluid to enter the chamber 106 and preventing the fluid from escaping the chamber 106. The permeable properties may have wicking, capillary action, diffusion, or other similar properties or processes, and are referred to herein as "permeable" and/or "wicking." Such "wicking" may not include absorption into the fluid permeable membrane. The fluid permeable membrane 116 may also wick the fluid generally towards an interior of the chamber 106. The fluid permeable membrane 116 may include any material that may wick the fluid. For example, the fluid permeable membrane 116 may include fabric, such as a gauze (e.g., a silk, linen, or cotton gauze), another soft fabric, or another smooth fabric. Forming the fluid permeable membrane 116 from gauze, soft fabric, and/or smooth fabric may reduce chaffing caused by the fluid collection device 102. In an example, the fluid permeable membrane 116 may include a one way flow fabric to prevent fluid from leaking from the chamber 106 through the fluid permeable membrane 116.

The fluid collection device 102 may include a fluid permeable support 130 disposed in the chamber 106. The fluid permeable support 130 is configured to support the fluid permeable membrane 116 since the fluid permeable membrane 116 may be formed from a foldable, flimsy, or otherwise easily deformable material. For example, the fluid permeable support 130 may be positioned such that the fluid permeable membrane 116 is disposed between the fluid permeable support 130 and the fluid impermeable barrier 104. As such, the fluid permeable support 130 may support and maintain the position of the fluid permeable membrane 116. The fluid permeable support 130 may be formed from any fluid permeable material that is less deformable than the fluid permeable membrane 116. For example, the fluid permeable support 130 may include a porous polymer (e.g., nylon, polyester, polyurethane, polyethylene, polypropylene, etc.) structure (e.g., spun fibers such as spun nylon fibers) or an open cell foam. The fluid permeable support 130 may also wick any fluids that enter the chamber 106 such that, for example, the fluids are removed from the opening 108 and directed towards the tube 118. In an example, the fluid permeable support 130 may be omitted from the fluid collection device 102.

In an embodiment, at least one of the fluid permeable membrane 116 or the fluid permeable support 130 may be a wicking material configured to wick any of the bodily fluids away from the opening 108, thereby preventing bodily fluids from escaping the chamber 106. The wicking material may not include absorption of the bodily fluids into the wicking material. Put another way, substantially no absorption of the bodily fluids into the wicking material may take place after the wicking material is exposed to the bodily fluids. While no absorption is desired, the term "substantially no absorption" may allow for nominal amounts of absorption of the bodily fluids into the wicking material (e.g., absorbency), such as about 10 wt % of the dry weight of the wicking material, about 7 wt %, about 5 wt %, about 3 wt %, about 2 wt %, about 1 wt %, or about 0.5 wt % of the dry weight of the wicking material.

In an embodiment, the fluid permeable membrane 116 and the fluid permeable support 130 may at least substantially completely fill the portions of the chamber 106 that are not occupied by the tube 118. In an embodiment, the fluid permeable membrane 116 and the fluid permeable support 130 do not substantially completely fill the portions of the chamber 106 that are not occupied by the tube 118. In such an embodiment, the fluid collection device 102 includes a reservoir 132 disposed in the chamber 106. The reservoir 132 is a substantially unoccupied portion of the chamber 106. The fluids that are in the chamber 106 may flow through the fluid permeable membrane 116 and/or fluid permeable support 130 to the reservoir 132. The reservoir 132 may store at least some of the fluids therein.

In an embodiment, the inlet of the tube 118 (e.g., distal tip of the tube 118) may be disposed in or near the reservoir 132. For example, the inlet of the tube 118 may be positioned in the reservoir 132 (as illustrated) or may be flush with the portions of the fluid permeable membrane 116 and/or fluid permeable support 130 that partially define the reservoir 132. In an embodiment, the inlet of the tube 118 may be spaced from the reservoir 132, for example, by at least a portion of the fluid permeable support 130.

In an example, the reservoir 132 may be located at and/or near the distal tip 126. However, the reservoir 132 may be located at different locations in the chamber 106. For example, the reservoir 132 may be located at and/or near the outlet 110. In another example, fluid collection device 102 may include multiple reservoirs, such as a first reservoir that is located at and/or near the distal tip 126 and a second reservoir at and/or near the outlet 110. In another example, the fluid permeable support 130 is spaced from at least a portion of the tube 118 and the reservoir 132 may be the space between the fluid permeable support 130 and the tube 118.

Figure 2:
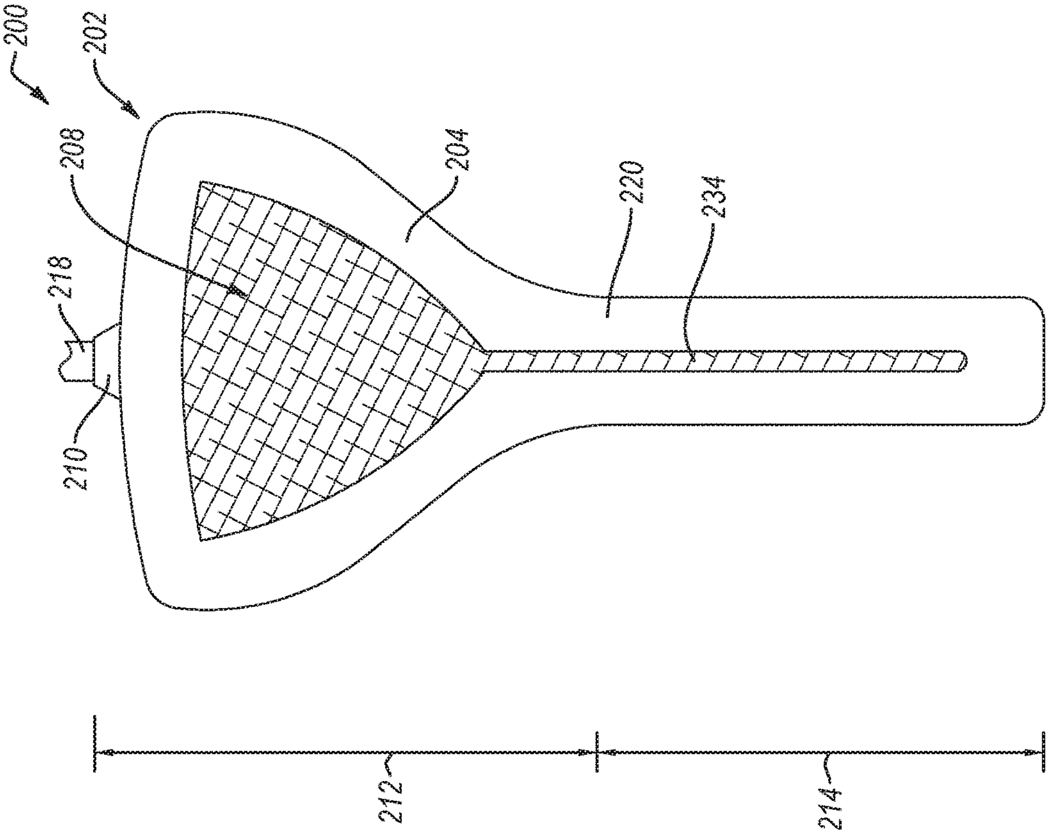
FIG. 2 is a top plan view of a portion of a fluid collection system, according to an embodiment.

FIG. 2 is a top plan view of a portion of a fluid collection system 200, according to an embodiment. Except as otherwise disclosed herein, the fluid collection system 200 is the same or substantially similar to any of the fluid collection systems disclosed herein. For example, the fluid collection system 200 may include a fluid collection device 202. The fluid collection device 202 includes a fluid impermeable barrier 204 defining a chamber (not shown), an opening 208, and an outlet 210 configured to receive a tube 218. The fluid collection device 202 also includes a fluid receiving portion 212 that defines the opening 208 and an longitudinal portion 214 extending from the fluid receiving portion 212.

The fluid collection device 202 also includes a slit 234. The slit 234 extends from the opening 208 and into the longitudinal portion 214. As such, the slit 234 is at least partially defined by the longitudinal portion 214 (e.g., the portion of the fluid impermeable barrier 204 that forms part of the fluid receiving portion 212). The slit 234 may be configured to receive fluid (e.g., urine or other bodily fluid) that is not received by the opening 208. For example, fluid that is not received by the opening 208 may trickle down the perineum of the individual since the groin channels the fluid towards the perineum when the individual is lying on the individual's back, sitting up, or standing. The slit 234 is positioned at or near the perineum of the individual since the longitudinal portion 214 is positioned at or near the perineum. This position of the slit 234 allows the slit 234 to receiving at least some of the fluid that trickles down the perineum.

In an embodiment, the slit 234 exhibits a width that is relatively narrow relative to the width of the longitudinal portion 214. For example, the slit 234 exhibits a width that is at most about 50% (e.g., at most about 40%, at most about 30%, at most about 20%, or in ranges of about 5% to about 20%, about 15% to about 30%, about 20% to about 40%, or about 30% to about 50%) the corresponding (i.e., parallel and overlapping) width of the longitudinal portion 214. The relatively narrow width of the slit 234 provides sufficient surface area for an adhesive to be applied to the front face 220 of the longitudinal portion 214. The width of the slit 234 may be selected based on the corresponding width of the longitudinal portion 214 because, generally, increasing the corresponding width of the longitudinal portion 214 allows for the width of the slit 234 to occupy a greater percentage of the corresponding width. However, it is noted that in some embodiments, the slit 234 may exhibit a width that is more than about 50% (e.g., 50% to about 75% or about 50% to about 60%) the corresponding width of the longitudinal portion 214.

In an embodiment, the slit 234 extends along a majority of the length of the longitudinal portion 214. In such an embodiment, the slit 234 may receive more fluid than if the slit 234 extending only along a small percentage (e.g., less than 50%) of the length of the longitudinal portion 214. However, in some embodiments, the slit 234 may only extend along a small percentage of the length of the longitudinal portion 214.

Figure 3:
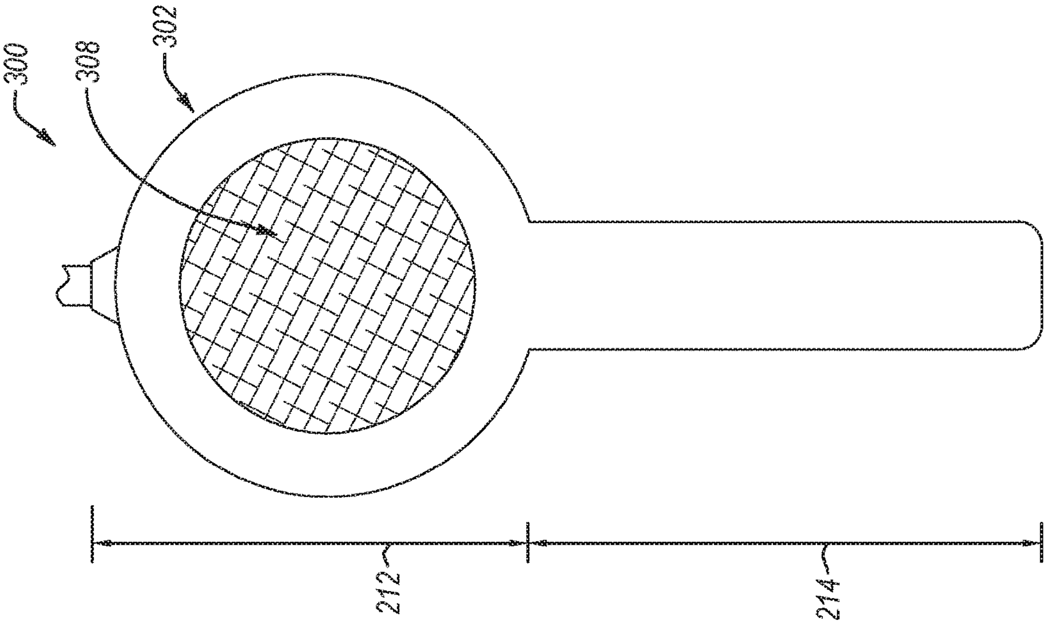
FIG. 3 is a top plan view of a portion of a fluid collection system, according to an embodiment.

The fluid receiving portions of the fluid collection devices illustrated in FIGS. 1A and 2 exhibit a generally triangular shape. However, as previously discussed, the fluid receiving portions of any of the fluid collection devices disclosed herein may exhibit any other suitable shape. For example, FIG. 3 is a top plan view of a portion of a fluid collection system 300, according to an embodiment. Except as otherwise disclosed herein, the fluid collection system 300 is the same as or substantially similar to any of the fluid collection systems disclosed herein. For example, the fluid collection system 300 includes a fluid collection device 302 that includes a fluid receiving portion 312 defining an opening 308 and an longitudinal portion 314 extending from the fluid receiving portion 312.

The fluid receiving portion 312 exhibits a generally circular shape. The generally circular shape of the fluid receiving portion 312 allows the opening 308 to exhibit a generally circular shape while also exhibiting a shape that corresponds to the shape of the fluid receiving portion 312. As previously discussed, allowing the opening 308 to exhibit the corresponding shape of the fluid receiving portion 312 allows the opening 308 to exhibit the largest possible size. Further, as previously discussed, the generally circular shape of the opening 308 may allow the fluid receiving portion 312 to be positioned such that the distance from the urethral opening to the edge of the opening 308 is substantially constant.

It is noted that the fluid receiving portions disclosed herein may exhibit other shapes. For example, the fluid receiving portions may exhibit a generally trapezoidal shape, a generally semicircular shape, a generally rectangular shape, a generally oval shape, or a generally pentagonal shape.

Figure 4:
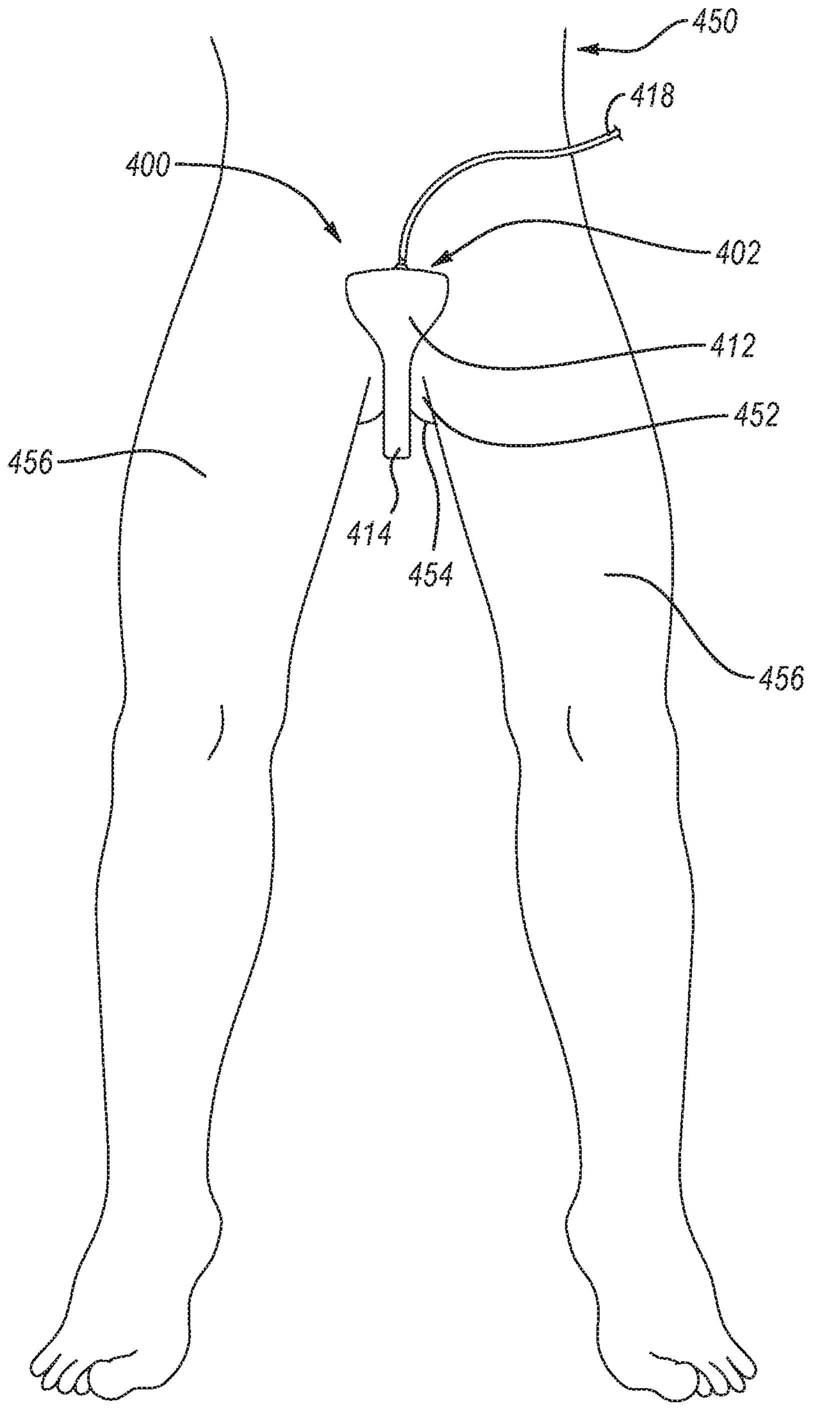
FIG. 4 is a front view of a urine collection system worn by an individual, according to an embodiment.

As previously discussed, the fluid collection devices disclosed herein may be positioned on an individual. FIG. 4 is a front view of a urine collection system 400 worn by an individual 450, according to an embodiment. Except as otherwise disclosed herein, the urine collection system 400 is the same or substantially similar to any of the urine collection systems disclosed herein. For example, the urine collection system 400 may include a fluid collection device 402 including a fluid receiving portion 412 and an longitudinal portion 414. In the illustrated embodiment, the fluid collection device 402 is the same or substantially similar to the fluid collection device 102 or 202 of FIGS. 1A-2. However, it is noted that the fluid collection device 402 may be the same or similar to any of the other fluid collection devices disclosed herein.

The individual 450 includes a groin 452, a perineum 454, and two thighs 456. In the illustrated embodiment, the thighs 456 of the individual 450 are illustrated as being separated such that the view of the fluid collection device 402 is unobstructed. However, there is no requirement that the thighs 456 of the individual 450 are separated and, in some embodiments, the thighs 456 of the individual 450 may need to contact each other or at least be positioned proximate to each other to maintain the position of the fluid collection device 402.

The fluid collection device 402 is positioned on the individual 450 such that the fluid receiving portion 412 is positioned adjacent to the urethral opening (not shown, obscured) of the individual 450. In other words, the fluid receiving portion 412 is positioned adjacent to the groin 452 of the individual 450. The longitudinal portion 414 is then positioned against and/or near the perineum 454 of the individual 450. This allows the fluid collection device 402 to receive fluid (e.g., urine) from the individual 450 and the maintain the position of the fluid collection device 402 relative to the individual 450, as discussed in more detail above.

Figure 5:
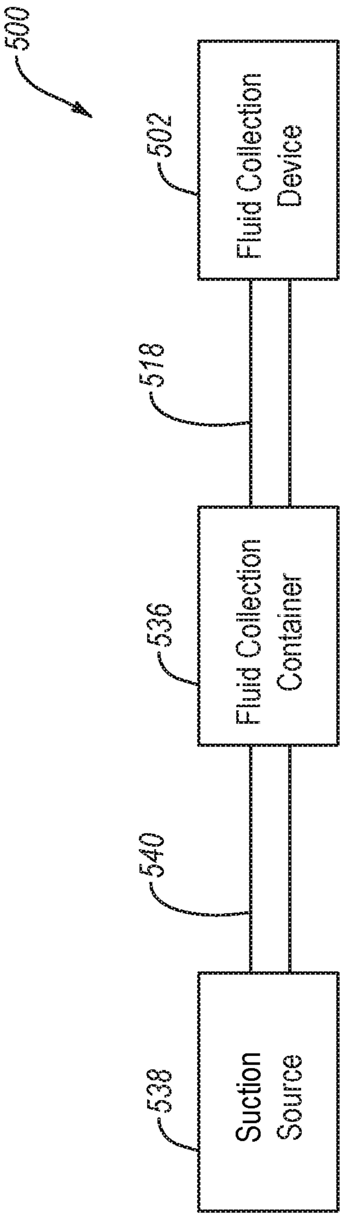
FIG. 5 is a schematic illustration of a fluid collection system, according to an embodiment.

FIG. 5 is a schematic illustrating of a fluid collection system 500, according to an embodiment. The fluid collection system 500 includes a fluid collection device 502 that is the same or substantially similar to any of the fluid collection devices disclosed herein. For example, the fluid collection device 502 may include a fluid receiving portion and an longitudinal portion. The fluid collection system 500 also include a fluid collection container 536 that is in indirectly fluid communication with the fluid collection device 502 via at least one first tube 518 (e.g., tube 118 or 218 of FIGS. 1A-2). The fluid collection container 536 may be positioned downstream from the fluid collection device 502. The fluid collection system 500 also includes a suction source 538 that is configured to apply a suction force (e.g., a continuous suction force) to the chamber of the fluid collection device 502 thereby removing fluid from the chamber and depositing the fluid in the fluid collection container 536. In the illustrated embodiment, the suction source 538 is vacuum source. In such an embodiment, the suction source 538 is positioned downstream from the fluid collection container 536 and may be in fluid communication with the fluid collection container 536 via at least one second tube 540. However, in an embodiment, the suction source 538 is a gas source that is positioned upstream from the fluid collection device 502. Examples of fluid collection systems that include gas sources are disclosed in PCT Application No. PCT/US2019/029609 filed on Apr. 29, 2019, the disclosure of which is incorporated herein, in its entirety, by this reference.

Figure 6:
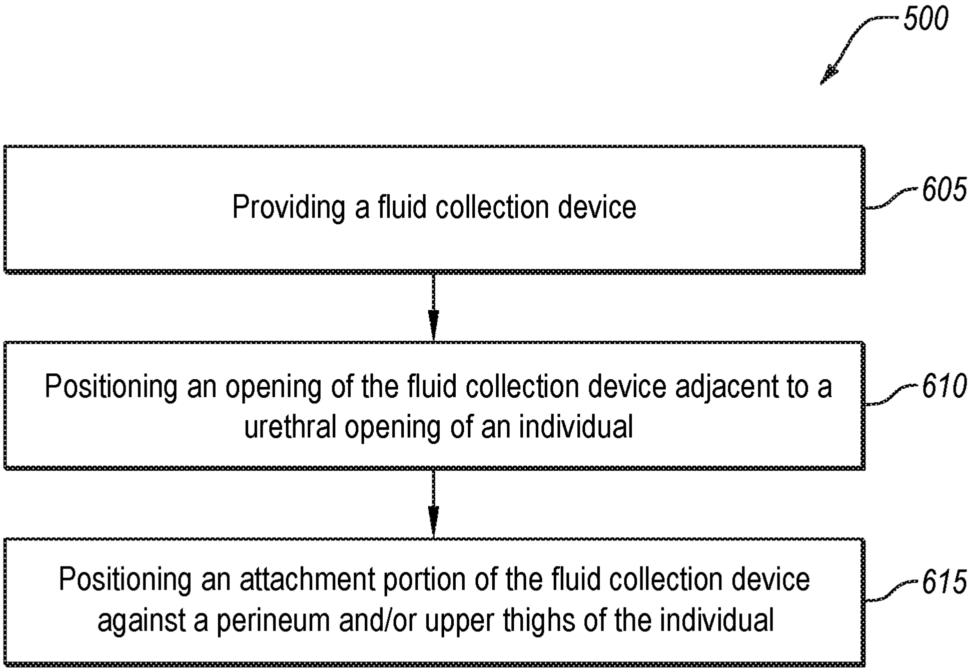
FIG. 6 is a flow diagram of a method to use any of the fluid collection devices and/or fluid collection systems disclosed herein, according to an embodiment.

FIG. 6 is a flow diagram of a method 600 to use any of the fluid collection devices and/or fluid collection systems disclosed herein, according to an embodiment. The method 600 may include act 605, which recites "providing a fluid collection device." Act 605 may be followed by act 610, which recites "positioning an opening of the fluid collection device adjacent to a urethral opening of an individual." Act 610 may be followed by act 615, which recites "positioning an longitudinal portion of the fluid collection device against a perineum and/or upper thighs of the individual."

Acts 605, 610, 615 of the method 600 are for illustrative purposes. For example, the act 605, 610, 615 of the method 600 may be performed in different orders, split into multiple acts, modified, supplemented, or combined. In an example, one or more of the acts 605, 610, 615 of the method 600 may be omitted from the method 600.

Act 605 recites "providing a fluid collection device." Act 605 includes providing any of the fluid collection devices disclosed herein. For example, act 605 may include providing a fluid collection device that includes a fluid impermeable barrier defining a chamber, an opening, and an outlet. The fluid collection device may also include a fluid permeable membrane extending across the opening. The fluid collection device may also include a fluid receiving portion that includes a portion of the fluid impermeable barrier that at least partially defines the opening and an longitudinal portion extending from the fluid receiving portion.

Act 610 recites "positioning an opening of the fluid collection device adjacent to a urethral opening of an individual." In an example, act 610 may include positioning the opening adjacent to a buried penis. In an example, act 610 may include positioning the opening adjacent to a female urethral opening or a non-buried penis.

Act 615 recites "positioning an longitudinal portion of the fluid collection device against a perineum and/or upper thighs of the individual." In an example, act 615 includes attaching the longitudinal portion against the perineum and/or upper thighs with an adhesive. In an example, act 615 includes attaching the longitudinal portion against the perineum and/or upper thighs by merely positioning the longitudinal portion at or near the perineum and allowing the contact between longitudinal portion and the thighs to hold the longitudinal portion in its position.

The method 600 may also include receiving fluids (e.g., urine) into the chamber. For example, a urethral opening may emit urine that contacts the fluid permeable membrane and the fluid permeable membrane may wick the urine into the chamber. A suction force may be applied to the chamber which may facilitate the fluid permeable membrane wicking the urine into the chamber. The urine that is wicked into the chamber may flow from the fluid permeable membrane towards at least one inlet of a tube that is disposed in the chamber. For example, the urine may flow from the fluid permeable membrane, through the fluid permeable support, into the fluid reservoir, and into the tube.

As previously discussed, a suction force may be applied to the chamber. The suction force may be a continuous suction force or a discontinuous suction force. The suction force may pull the fluids that are present in the chamber into the tube, through the tube, to the fluid collection container, and deposit the fluid in the fluid collection container.

Terms of degree (e.g., "about," "substantially," "generally," etc.) indicate structurally or functionally insignificant variations. In an example, when the term of degree is included with a term indicating quantity, the term of degree is interpreted to mean±10%, ±5%, ±2%, or 0% of the term indicating quantity. In an example, when the term of degree is used to modify a shape, the term of degree indicates that the shape being modified by the term of degree has the appearance of the disclosed shape. For instance, the term of degree may be used to indicate that the shape may have rounded corners instead of sharp corners, curved edges instead of straight edges, one or more protrusions extending therefrom, is oblong, is the same as the disclosed shape, etc.

While various aspects and embodiments have been disclosed herein, other aspects and embodiments are contemplated. The various aspects and embodiment disclosed herein are for purposes of illustration and are not intended to be limiting.

We claim:

1. A fluid collection device, comprising:

a fluid impermeable barrier defining a chamber, an opening, and an outlet;

a fluid permeable membrane extending across the opening;

a fluid receiving portion including a portion of the fluid impermeable barrier that defines all of or a substantial majority of the opening; and a longitudinal portion configured to be positioned against a perineum of an individual, the longitudinal portion exhibiting an oblong shape and extending from the fluid receiving portion in a direction that is parallel to a longitudinal axis of the longitudinal portion, the longitudinal portion forming a distal end region that is positioned closer to the perineum of the individual than the fluid receiving portion during use;

wherein the fluid collection device exhibits a maximum length measured from a distal tip of the longitudinal portion to an opposing portion of the fluid receiving portion;

wherein the fluid receiving portion exhibits a first maximum width measured perpendicular to the maximum length, and the longitudinal portion exhibits a second maximum width measured parallel to the first maximum width, and wherein the first maximum width is greater than the second maximum width; and wherein the chamber is defined by the fluid receiving portion and the longitudinal portion.

2. The fluid collection device of claim 1, wherein the fluid impermeable barrier includes silicone.

3. The fluid collection device of claim 1, wherein the fluid receiving portion exhibits a generally triangular shape, and wherein the longitudinal portion extends from a vertex of the generally triangular shape.

4. The fluid collection device of claim 1, wherein the fluid receiving portion exhibits a generally circular shape.

5. The fluid collection device of claim 1, wherein the longitudinal portion exhibits a length measured from the distal tip of thereof to an intersection of the longitudinal portion and the fluid receiving portion that is at least 10 cm.

6. The fluid collection device of claim 1, wherein the second maximum width is about 2 cm to about 6 cm.

7. The fluid collection device of claim 1, wherein the longitudinal portion at least partially defines a slit extending from the opening.

8. The fluid collection device of claim 1, further comprising a fluid permeable support disposed in the chamber and supporting the fluid permeable membrane.

9. The fluid collection device of claim 1, further comprising a tube positioned through the outlet.

10. The fluid collection device of claim 9, wherein an inlet of the tube is disposed in a substantially unoccupied fluid reservoir.

11. The fluid collection device of claim 10, wherein the longitudinal portion defines the substantially unoccupied reservoir at or near the distal tip thereof.

12. A fluid collection system, comprising:

a fluid collection device including:

a fluid impermeable barrier defining a chamber, an opening, and an outlet;

a fluid permeable membrane extending across the opening;

a fluid receiving portion including a portion of the fluid impermeable barrier that defines all of or a substantial majority of the opening; and a longitudinal portion exhibiting an oblong shape and extending from the fluid receiving portion in a direction that is parallel to a longitudinal axis of the longitudinal portion;

wherein the fluid collection device exhibits a maximum length measured from a distal tip of the longitudinal portion to an opposing portion of the fluid receiving portion; and wherein the fluid receiving portion exhibits a first maximum width measured perpendicular to the maximum length, and the longitudinal portion exhibits a second maximum width measured parallel to the first maximum width, and wherein the first maximum width is greater than the second maximum width; and wherein the chamber is defined by the fluid receiving portion and the longitudinal portion;

a fluid collection container in fluid communication with and positioned downstream from the fluid collection device;

a suction source in fluid communication with the fluid collection device and the fluid collection container; and at least one tube that allows the fluid collection device to be in fluid communication with the fluid collection container and the suction source.

13. The fluid collection system of claim 12, wherein the suction source is configured to provide a continuous suction force to the fluid collection device.

14. The fluid collection system of claim 12, wherein the suction source is a vacuum source positioned downstream from the fluid collection container.

15. A method, comprising:

providing a fluid collection device, the fluid collection device including:

a fluid impermeable barrier defining a chamber, an opening, and an outlet;

a fluid permeable membrane extending across the opening;

a fluid receiving portion including a portion of the fluid impermeable barrier that defines all of or a substantial majority of the opening; and a longitudinal portion exhibiting an oblong shape and extending from the fluid receiving portion in a direction that is parallel to a longitudinal axis of the longitudinal portion;

wherein the fluid collection device exhibits a maximum length measured from a distal tip of the longitudinal portion to an opposing portion of the fluid receiving portion;

wherein the fluid receiving portion exhibits a first maximum width measured perpendicular to the maximum length, and the longitudinal portion exhibits a second maximum width measured parallel to the first maximum width, and wherein the first maximum width is greater than the second maximum width; and wherein the chamber is defined by the fluid receiving portion and the longitudinal portion;

positioning the opening of the fluid collection device adjacent to a urethral opening of an individual; and positioning the longitudinal portion against a perineum and/or upper thighs of the individual.

16. The method of claim 15, wherein positioning the opening of the fluid collection device adjacent to a urethral opening of an individual includes positioning the opening of the fluid collection device adjacent to a buried penis.

17. The method of claim 15, wherein positioning the opening of the fluid collection device adjacent to a urethral opening of an individual includes positioning the opening of the fluid collection device adjacent to a female urethra.

18. The method of claim 15, wherein positioning the longitudinal portion of the fluid impermeable barrier against the perineum and/or upper thighs of the individual includes attaching the longitudinal portion of the fluid impermeable barrier to the perineum and/or the upper thighs with an adhesive.

19. The method of claim 15, further comprising receiving fluid from the urethral opening into the chamber.

20. The method of claim 15, further comprising removing at least some of the fluid from the chamber and disposing the at least some of the fluid in a fluid collection container using a suction force, wherein the suction force is provided by a suction source.

21. The fluid collection device of claim 3, wherein the outlet is in a portion of the fluid receiving portion opposite the vertex of the generally triangular shape from which the longitudinal portion extends.

22. The fluid collection device of claim 1, wherein substantially all of the fluid receiving portion exhibits a shape that generally corresponds to the shape of the opening except for a portion of the fluid receiving portion defining the outlet.

23. The fluid collection device of claim 1, wherein substantially all of the fluid receiving portion exhibits a width that is greater than the second maximum width of the longitudinal portion.

24. The fluid collection device of claim 1, wherein a width of fluid receiving portion continuously increases from an intersection of the fluid receiving portion and the longitudinal portion to the first maximum width.

* * * * *